United States Patent
Cully et al.

(10) Patent No.: US 11,173,281 B2
(45) Date of Patent: Nov. 16, 2021

(54) FENESTRATION DEVICES, SYSTEMS, AND METHODS

(71) Applicant: W. L. Gore & Associates, Inc., Newark, DE (US)

(72) Inventors: Edward H. Cully, Flagstaff, AZ (US); Sherif A. Eskaros, Elkton, MD (US); Eric A. Mokelke, Flagstaff, AZ (US); Reed A. Houge, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 204 days.

(21) Appl. No.: 16/011,279

(22) Filed: Jun. 18, 2018

(65) Prior Publication Data

US 2018/0361118 A1 Dec. 20, 2018

Related U.S. Application Data

(60) Provisional application No. 62/521,724, filed on Jun. 19, 2017.

(51) Int. Cl.
| | | |
|---|---|---|
| *A61M 25/00* | (2006.01) | |
| *A61B 17/3203* | (2006.01) | |
| *A61B 17/04* | (2006.01) | |
| *A61B 17/12* | (2006.01) | |
| *A61F 2/95* | (2013.01) | |

(Continued)

(52) U.S. Cl.
CPC ..... *A61M 25/0084* (2013.01); *A61B 17/0469* (2013.01); *A61B 17/12013* (2013.01);
(Continued)

(58) Field of Classification Search
CPC ...... A61M 25/0084; A61M 2025/0093; A61M 2025/0095; A61M 2025/0096;
(Continued)

(56) References Cited

U.S. PATENT DOCUMENTS

| | | | | |
|---|---|---|---|---|
| 6,599,267 B1* | 7/2003 | Ray | ............... | A61M 25/0074 604/102.01 |
| 6,673,070 B2* | 1/2004 | Edwards | ............ | A61B 18/1477 606/41 |

(Continued)

FOREIGN PATENT DOCUMENTS

| | | |
|---|---|---|
| EP | 2640452 A1 | 1/2018 |
| JP | 2002-503512 A | 2/2002 |

(Continued)

OTHER PUBLICATIONS

Foam System for Acute Hemorrhage, Arsenal Medical, 2015, 1 page http://arsenalmedical.com/foam-system-acute-hemorrhage.

(Continued)

*Primary Examiner* — Tuan V Nguyen

(57) ABSTRACT

An endoluminal access device including an outer sheath defining a lumen and a guide assembly. The guide assembly includes an expandable portion configured to be transitioned between a collapsed configuration having a first diameter and an expanded configuration having a second diameter that is greater than the first diameter. The expandable portion includes a first arm defining a first lumen and an aperture in communication with the first lumen. The expandable portion is configured to expand outwardly from a central longitudinal axis when the expandable portion transitions to the expanded configuration and to deflect inwardly toward the central longitudinal axis when the expandable portion is transitioned to the collapsed configuration. The endoluminal access device further includes an endoluminal tool deliverable from the first lumen of the first arm and outwardly from the aperture of the first arm.

27 Claims, 16 Drawing Sheets

(51) Int. Cl.
| | |
|---|---|
| *A61B 18/14* | (2006.01) |
| *A61M 5/00* | (2006.01) |
| *A61B 17/34* | (2006.01) |
| *A61B 17/32* | (2006.01) |
| *A61B 17/00* | (2006.01) |
| *A61M 25/04* | (2006.01) |
| *A61B 18/00* | (2006.01) |
| *A61B 17/22* | (2006.01) |
| *A61B 17/068* | (2006.01) |

(52) U.S. Cl.
CPC .... *A61B 17/12186* (2013.01); *A61B 17/3203* (2013.01); *A61B 17/3478* (2013.01); *A61B 18/1492* (2013.01); *A61F 2/95* (2013.01); *A61M 5/00* (2013.01); *A61M 25/007* (2013.01); *A61M 25/0074* (2013.01); *A61B 17/068* (2013.01); *A61B 17/1204* (2013.01); *A61B 2017/00336* (2013.01); *A61B 2017/00557* (2013.01); *A61B 2017/00783* (2013.01); *A61B 2017/0472* (2013.01); *A61B 2017/1205* (2013.01); *A61B 2017/22095* (2013.01); *A61B 2017/320052* (2013.01); *A61B 2018/00404* (2013.01); *A61B 2018/00601* (2013.01); *A61M 25/04* (2013.01); *A61M 2025/0087* (2013.01)

(58) Field of Classification Search
CPC .......... A61B 17/12186; A61B 17/0469; A61B 17/3203; A61B 2017/320052; A61F 2/95
See application file for complete search history.

(56) References Cited

U.S. PATENT DOCUMENTS

| | | | |
|---|---|---|---|
| 2002/0026217 A1 | 2/2002 | Baker et al. | |
| 2003/0023248 A1 | 1/2003 | Parodi | |
| 2004/0068276 A1* | 4/2004 | Golden | A61B 17/115 606/153 |
| 2005/0192599 A1* | 9/2005 | Demarais | A61B 17/12022 606/151 |
| 2007/0270757 A1* | 11/2007 | Willis | A61M 25/1006 604/173 |
| 2011/0054381 A1 | 3/2011 | Van Dam | |
| 2012/0059309 A1* | 3/2012 | di Palma | A61M 25/007 604/22 |
| 2012/0136385 A1 | 5/2012 | Cully | |
| 2015/0094747 A1 | 4/2015 | Boland | |

FOREIGN PATENT DOCUMENTS

| | | |
|---|---|---|
| JP | 2002-526193 A | 8/2002 |
| JP | 2013-521016 A | 6/2013 |
| WO | WO-1999/042047 | 8/1999 |
| WO | WO-9942044 | 8/1999 |
| WO | WO-2007082343 A1 | 7/2007 |
| WO | WO-2009013463 | 1/2009 |

OTHER PUBLICATIONS

Single-Pulse and Unidirectional Electrical Activation of the Cervical Vagus Nerve Reduces Tumor Necrosis Factor in Endotoxemia Published May 13, 2015. 6 pages. Accessed on Nov. 1, 2018.
International Search Report and Written Opinion from PCT/US2018/038323 dated Aug. 31, 2018, 15 pages.
"Research Suggests that Low-Level Vagus Nerve Stimulation May Help Reduce Inflammation," The Feinstein Institute for Medical Research and SetPoint Medical Inc, May 21, 2015. http://www.ptproductsonline.com/2015/05/research-suggests-low-level-vagus-nerve-stimulation-may-help-reduce-inflammation/.
International Preliminary Report on Patentability received for PCT Patent Application No. PCT/US2018/038323, dated Jan. 2, 2020, 9 pages.

\* cited by examiner

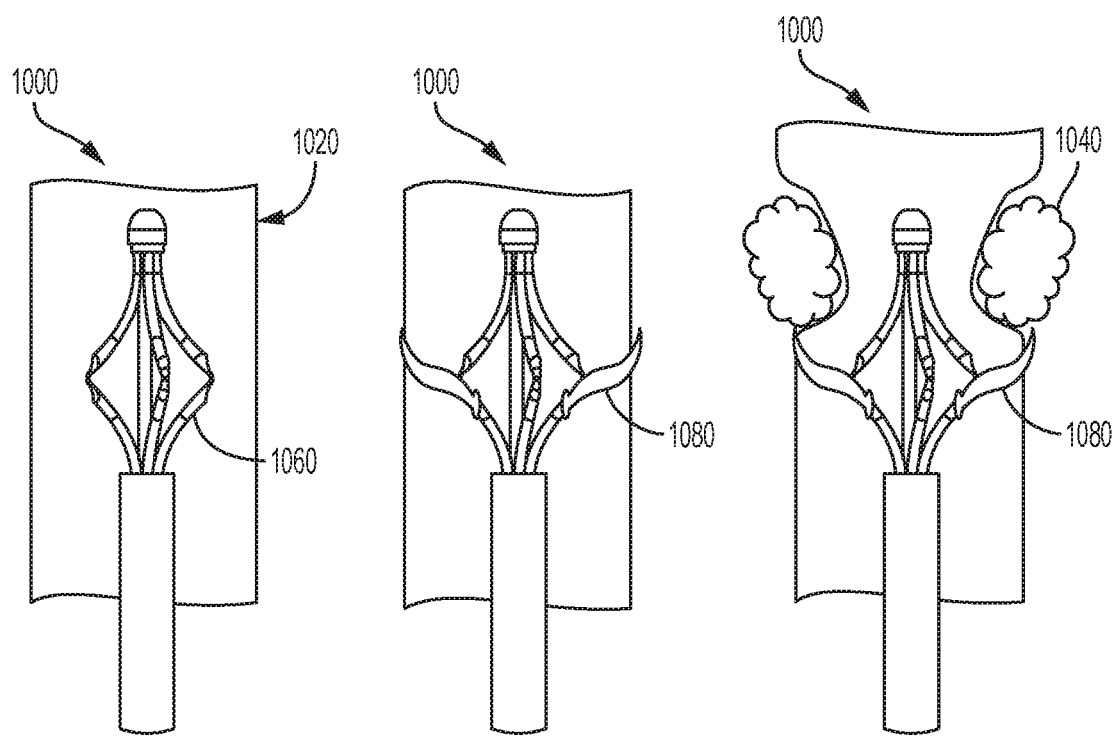
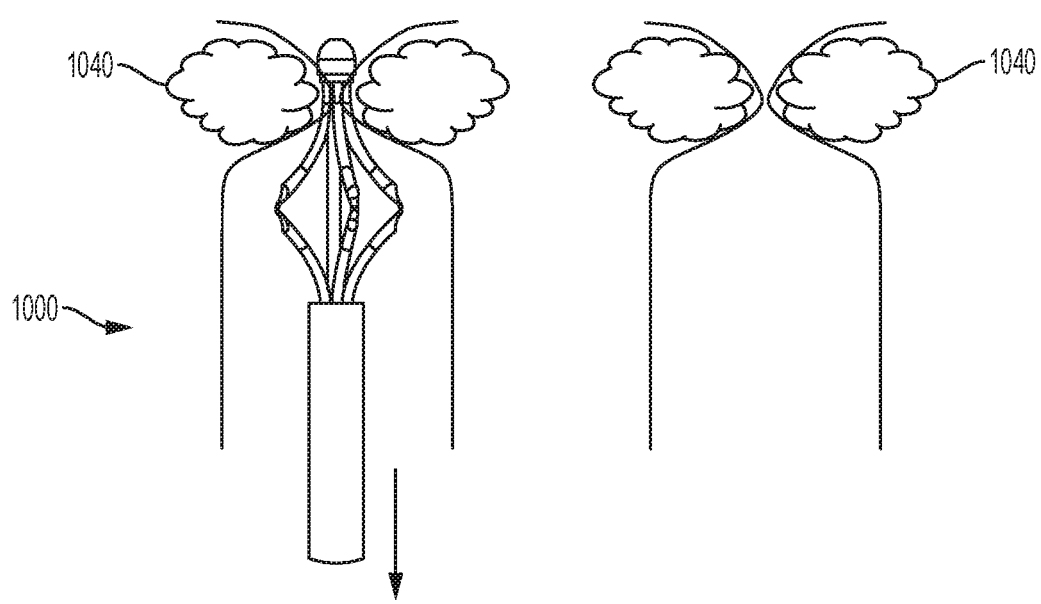
FIG. 16A  FIG. 16B  FIG. 16C
FIG. 16D  FIG. 16E

FENESTRATION DEVICES, SYSTEMS, AND METHODS

CROSS-REFERENCE TO RELATED APPLICATION

This application claims the benefit of Provisional Application No. 62/521,724, filed Jun. 19, 2017, which is incorporated herein by reference in its entirety for all purposes.

TECHNICAL FIELD

The present disclosure relates generally to systems, methods and devices for guiding tools to a desired orientation during medical procedures. More specifically, the present disclosure relates to systems, methods, and devices for endoluminal and/or percutaneous delivery of tools for patient treatment, including both endoluminal/percutaneous vascular applications and endoluminal/percutaneous treatment of other organs, such as those associated with respiratory, gastrointestinal, or urological treatments, for example.

BACKGROUND

Minimally invasive procedures can include both percutaneous and/or endoluminal procedures. Endoluminal surgery is typically a minimally invasive method of treatment that is preferred for many types of procedures. In the case of the vasculature, for example, endoluminal surgery includes endovascular treatment of vascular diseases. Endovascular treatment is generally accomplished via access to a treatment site from inside the vasculature. Certain difficulties with endoluminal procedures include traversing the irregularly shaped, tortuous, branched, and narrow lumens of the body to gain access to desired treatment sites within the body. Once access to a treatment site is gained, difficulties may include fine-tuning the rotational and lateral position of the tools or other devices at the treatment site. It may also be difficult to maintain lumen patency (e.g., blood flow through blood vessels) during the course of treatment.

SUMMARY

Disclosed herein is an endoluminal access device. The endoluminal access device includes an outer sheath defining a lumen and a guide assembly. The guide assembly includes an expandable portion configured to be transitioned between a collapsed configuration having a first diameter and an expanded configuration having a second diameter that is greater than the first diameter. The expandable portion includes a first arm defining a first lumen and an aperture in communication with the first lumen. The expandable portion is configured to expand outwardly from a central longitudinal axis when the expandable portion transitions to the expanded configuration and to deflect inwardly toward the central longitudinal axis when the expandable portion is transitioned to the collapsed configuration. The endoluminal access device further includes an endoluminal tool deliverable from the first lumen of the first arm and outwardly from the aperture of the first arm.

Also disclosed herein is a device for accessing a vessel surface from inside the vessel. The device has a central longitudinal axis and comprises an outer sheath defining a guide lumen; and a guide assembly slidably deployable from within the outer sheath and having an expandable portion. The expandable portion includes a plurality of arms. A first arm of the plurality of arms has a length, a wall defining a first lumen along the length, and an aperture in communication with the first lumen. The expandable portion is transitionable between a collapsed configuration with the first arm linear along the central longitudinal axis and an expanded configuration with a portion of the first arm expanded outward from the central longitudinal axis. The aperture is located on the first arm such that in the expanded configuration the aperture is positioned on the portion of the first arm that is expanded outward from the central longitudinal axis.

Also disclosed herein is a method of deploying an endoluminal tool within a lumen. The method comprises inserting a guide device through a lumen of a vessel to a treatment site. The guide device includes a guide sheath having an outer diameter, and an expandable portion having a first outer diameter in a collapsed configuration. The method further includes deploying the expandable portion from within the guide sheath and expanding the expandable portion from the first outer diameter to a second outer diameter that is larger than the outer diameter of the guide sheath such that a first arm of the expandable portion has an aperture at a section of the first arm that is at an outermost location from a central longitudinal axis of the expandable portion. The method further includes deploying an endoluminal tool from the first arm such that the endoluminal tool extends at an escape angle outward from the central longitudinal axis.

According to an example ("Example 1") an endoluminal access device includes an outer sheath defining a lumen and a guide assembly. The guide assembly includes an expandable portion configured to be transitioned between a collapsed configuration having a first diameter and an expanded configuration having a second diameter that is greater than the first diameter. The expandable portion includes a first arm defining a first lumen and an aperture in communication with the first lumen, the expandable portion being configured to expand outwardly from a central longitudinal axis when the expandable portion transitions to the expanded configuration and to deflect inwardly toward the central longitudinal axis when the expandable portion is transitioned from the expanded configuration to the collapsed configuration. The device also includes an endoluminal tool deliverable from the first lumen of the first arm and outwardly from the aperture of the first arm.

According to another example ("Example 2") further to Example 1, the endoluminal tool is slidably received within the first lumen.

According to another example ("Example 3") further to Example 1, the endoluminal tool is slidably delivered from within the first lumen through the aperture.

According to another example ("Example 4") further to Example 1, the first arm biases the endoluminal tool in a direction perpendicular to the central longitudinal axis of the expandable portion when the expandable portion is transitioned to the expanded configuration.

According to another example ("Example 5") further to Example 1, the endoluminal tool is configured to exit the aperture at an acute angle relative to the central longitudinal axis of the expandable portion when the expandable portion is transitioned to the expanded configuration.

According to another example ("Example 6") further to Example 1, in the expanded configuration, the aperture orients the endoluminal tool at an escape angle relative to the central longitudinal axis of the expandable portion.

According to another example ("Example 7") further to Example 1, in the expanded configuration the aperture orients the endoluminal tool at an escape angle from about 0 degrees to about 90 degrees relative to the central longitudinal axis of the expandable portion.

According to another example ("Example 8") further to Example 1, in the expanded configuration the aperture is configured to orient the endoluminal tool at an escape angle of any one of about 0 degrees, about 10 degrees, about 20 degrees, about 30 degrees, about 40 degrees, about 50 degrees, about 60 degrees, about 70 degrees, about 80 degrees, or about 90 degrees.

According to another example ("Example 9") further to Example 1, the endoluminal tool is a needle.

According to another example ("Example 10") further to Example 1, the expandable portion is configured to confront a barrier located outward from the expandable portion when the expandable portion is transitioned to the expanded configuration.

According to another example ("Example 11") further to Example 1, the expandable portion includes a plurality of arms that expand outwardly from the central longitudinal axis of the expandable portion when the expandable portion is transitioned to the expanded configuration.

According to another example ("Example 12") further to Example 11, the plurality of arms is configured to expand symmetrically from the central longitudinal axis of the expandable portion.

According to another example ("Example 13") further to Example 11, in the expanded configuration, each arm of the plurality of arms is spaced from another arm of the plurality of arms to define a plurality of open spaces between the plurality of arms.

According to another example ("Example 14") further to Example 11, the expandable portion includes gaps between individual arms of the plurality of arms and defines an open interior space through which fluid can flow when the expandable portion is transitioned to the expanded configuration.

According to another example ("Example 15") further to Example 11, the plurality of arms defines multiple lumens. Each lumen of the multiple lumens is configured to receive an endoluminal tool.

According to another example ("Example 16") further to Example 1, the fluid flow is maintained through the vessel with the endoluminal access device inserted within the vessel.

According to another example ("Example 17") further to Example 16, each lumen of the multiple lumens is configured to be remotely deflected in-situ and position the endoluminal tool received within each lumen.

According to another example ("Example 18") further to Example 1, the endoluminal tool is at least one of an infusion needle, a biopsy punch, a biopsy needle, an endotack, a suture device, a fixation device, a radiopaque marker, an occlusion coil, or a sensor.

According to another example ("Example 19") a device for accessing a vessel surface from inside a vessel has a central longitudinal axis and includes an outer sheath defining a guide lumen. The device also includes a guide assembly slidably deployable from within the outer sheath. The guide assembly has an expandable portion including a plurality of arms. The plurality of arms includes a first arm having a first end portion, a second end portion, a length, a wall defining a first lumen along the length, and an aperture in communication with the first lumen. The expandable portion is transitionable between a collapsed configuration with the first arm extending linearly along the central longitudinal axis and an expanded configuration with a portion of the first arm expanded outward from the central longitudinal axis. The aperture located on the first arm is such that, in the expanded configuration, the aperture is positioned on the portion of the first arm that is expanded outward from the central longitudinal axis.

According to another example ("Example 20") further to Example 19, the first arm defines a free end at the second end portion and in the expanded configuration the second end portion is expanded outwardly from the central longitudinal axis greater than an outer diameter of the outer sheath.

According to another example ("Example 21") further to Example 19, the first arm is configured to transition to the expanded configuration in response to the expandable portion being slidably advanced from within the outer sheath.

According to another example ("Example 22") further to Example 19, the first arm has an intermediate portion between the first end portion and the second end portion. The expanded configuration of the intermediate portion expands outward from the central longitudinal axis to a greater extent than an outer diameter of the outer sheath.

According to another example ("Example 23") further to Example 19, the device also includes an inner shaft having a distal end connected to the second end portion of the first arm. Drawing the distal end of the inner shaft toward the first end portion of the first arm transitions the expandable portion to the expanded configuration.

According to another example ("Example 24") further to Example 19, the device also includes a shaft portion connected to the expandable portion. The shaft portion defines an inner lumen and at least a first radial lumen, the inner shaft being slidably receivable within the inner lumen, and the first arm connected to the first radial lumen.

According to another example ("Example 25") further to Example 19, the device also includes an inflatable member located within an interior space defined by the plurality of arms, the inflatable member transitionable from a first outer diameter to a second outer diameter by inflating the inflatable member.

According to another example ("Example 26") further to Example 25, inflating the inflatable member expands the inflatable member to the second outer diameter and transitions the expandable portion from the collapsed configuration to the expanded configuration.

According to another example ("Example 27") further to Example 19, the device also includes an endoluminal tool deployable from the first arm outward from the central longitudinal axis.

According to another example ("Example 28") further to Example 19, the expandable portion is configured to deploy an endoluminal tool at an angle between 0 degrees and 90 degrees from the central longitudinal axis.

According to another example ("Example 29") further to Example 19, fluid flow is maintained through a vessel with the device inserted within the vessel.

According to another example ("Example 30") further to Example 19, the expandable portion includes gaps between individual arms of the plurality of arms and defines an open interior space through which fluid can flow when the expandable portion is transitioned to the expanded configuration.

According to another example ("Example 31") a method of deploying an endoluminal tool within a lumen includes inserting a guide device through a lumen of a vessel to a treatment site. The guide device includes a guide sheath having an outer diameter and an expandable portion having a first outer diameter in a collapsed configuration. The method also includes deploying the expandable portion from within the guide sheath. The method also includes expanding the expandable portion from the first outer diameter to a second outer diameter that is larger than the outer diameter of the guide sheath such that a first arm of the expandable portion has an aperture at a section of the first arm that is at an outermost location from a central longitudinal axis of the expandable portion. The method also includes deploying an endoluminal tool from the first arm such that the endoluminal tool extends at an escape angle outward from the central longitudinal axis.

According to another example ("Example 32") further to Example 31, deploying the expandable portion includes slidably extending the expandable portion from an opening at a distal end of the guide device, and wherein deploying the expandable portion causes the expandable portion to expand.

According to another example ("Example 33") further to Example 31, the guide device includes an inner shaft having a second end. The first arm of the expandable portion has a first portion, a second end portion attached to the second end of the inner shaft, and an intermediate portion between the first and second end portion. Deploying the expandable portion includes actuating the inner shaft such that the second end portion of the first arm is brought toward the first portion along the central longitudinal axis such that the intermediate portion expands outward from the central longitudinal axis.

According to another example ("Example 34") further to Example 31, at least some fluid flow is maintained through the lumen of the vessel throughout the steps of inserting the guide device, deploying the expandable portion, expanding the expandable portion, and deploying the endoluminal tool.

According to another example ("Example 35") further to Example 31, deploying the endoluminal tool includes deploying the endoluminal tool at an angle between 0 degrees and 90 degrees from the central longitudinal axis.

According to another example ("Example 36") further to Example 31, the endoluminal tool is deployed to access any one of an inside surface or an outside surface of the vessel.

According to another example ("Example 37") further to Example 31, the guide device is deployed to repeatedly deflect a needle from the guide device to firm a first path and insert a guide wire along the first path.

According to another example ("Example 38") further to Example 31, the guide device is deployed to simultaneously delivering multiple endotacks to a vessel wall.

According to another example ("Example 39") further to Example 31, the guide device is deployed to create a hydro-dissection within a lamina of a vessel wall.

According to another example ("Example 40") further to Example 39, the guide device is further deployed to deliver a multi-component substance to the hydro-dissection within a lamina of the vessel wall.

According to another example ("Example 41") a device or method of modifying an anatomy of a body lumen includes inserting a guide device through a lumen of a vessel to a treatment site. The guide device includes a guide sheath having an outer diameter and an expandable portion having a first outer diameter in a collapsed configuration. The method also includes deploying the expandable portion from within the guide sheath. The method also includes expanding the expandable portion from the first outer diameter to a second outer diameter that is larger than the first outer diameter of the guide sheath such that a first arm of the expandable portion has an aperture at a section of the first arm that is at an outermost location from a central longitudinal axis of the expandable portion. The method also includes deploying an endoluminal tool from the first arm such that the endoluminal tool extends at an escape angle outward from the central longitudinal axis. The method also includes piercing an inner wall of the lumen with the endoluminal tool such that a tip of the endoluminal tool is positioned outside of the lumen. The method also includes delivering a therapeutic agent to an abluminal side of the lumen.

According to another example ("Example 42") further to Example 41, the therapeutic agent is at least one of an occlusive material, a self-hardening gel, and a self-expanding gel.

According to another example ("Example 43") further to Example 41, the therapeutic agent imparts a pressure on an abluminal surface of the lumen such that a diameter of the lumen is reduced.

According to another example ("Example 44") further to Example 43, the pressure on the abluminal surface of the lumen is sufficient to collapse and occlude the lumen.

According to another example ("Example 45") further to Example 41, the treatment site includes at least one of a circulatory system, a venous system, a digestive system, and a urinary system.

According to another example ("Example 46") further to Example 41, wherein inserting the guide device includes inserting the guide device through a lumen of the vessel to the treatment site near a valve, and wherein delivering the therapeutic agent includes reducing the diameter of the lumen near the valve and biasing the valve in a closed position.

According to another example ("Example 47") further to Example 41, delivering the therapeutic agent includes delivering the therapeutic agent to restrict an aorta distal to at least one renal artery to reduce flow into the one or more side branches off the aorta by 20%-30% to improve kidney perfusion and diuresis.

According to another example ("Example 48") a device or method for treating an aneurysm includes inserting a guide device through a lumen of a vessel to a treatment site within the aneurysm. The guide device includes a guide sheath having an outer diameter and an expandable portion having a first outer diameter in a collapsed configuration. The method also includes deploying the expandable portion from within the guide sheath. The method also includes expanding the expandable portion from the first outer diameter to a second outer diameter that is larger than the first outer diameter of the guide sheath such that a first arm and a second arm of the expandable portion having an aperture at a section of the first arm and the second arm that is at an outermost location from a central longitudinal axis of the expandable portion. The method also includes deploying a first endoluminal tool from the first arm and a second endoluminal tool from the second arm such that the endoluminal tools extend at an escape angle outward from the central longitudinal axis. The method also includes piercing an inner wall of the aneurysm with the first and second endoluminal tools such that ends of the endoluminal tools are positioned outside of the wall. The method also includes delivering a therapeutic agent through the first and second endoluminal tools to an abluminal side of the lumen to substantially surround the aneurysm.

According to another example ("Example 49") further to Example 48, the therapeutic agent is a self-hardening gel.

According to another example ("Example 50") further to Example 48, delivering the therapeutic agent prevents further expansion of the aneurysm.

BRIEF DESCRIPTION OF THE DRAWINGS

FIGS. 16A to 16E are schematic views illustrating a method of delivering an occlusive agent to an area outside of a vessel, according to various examples.

Figure 1:
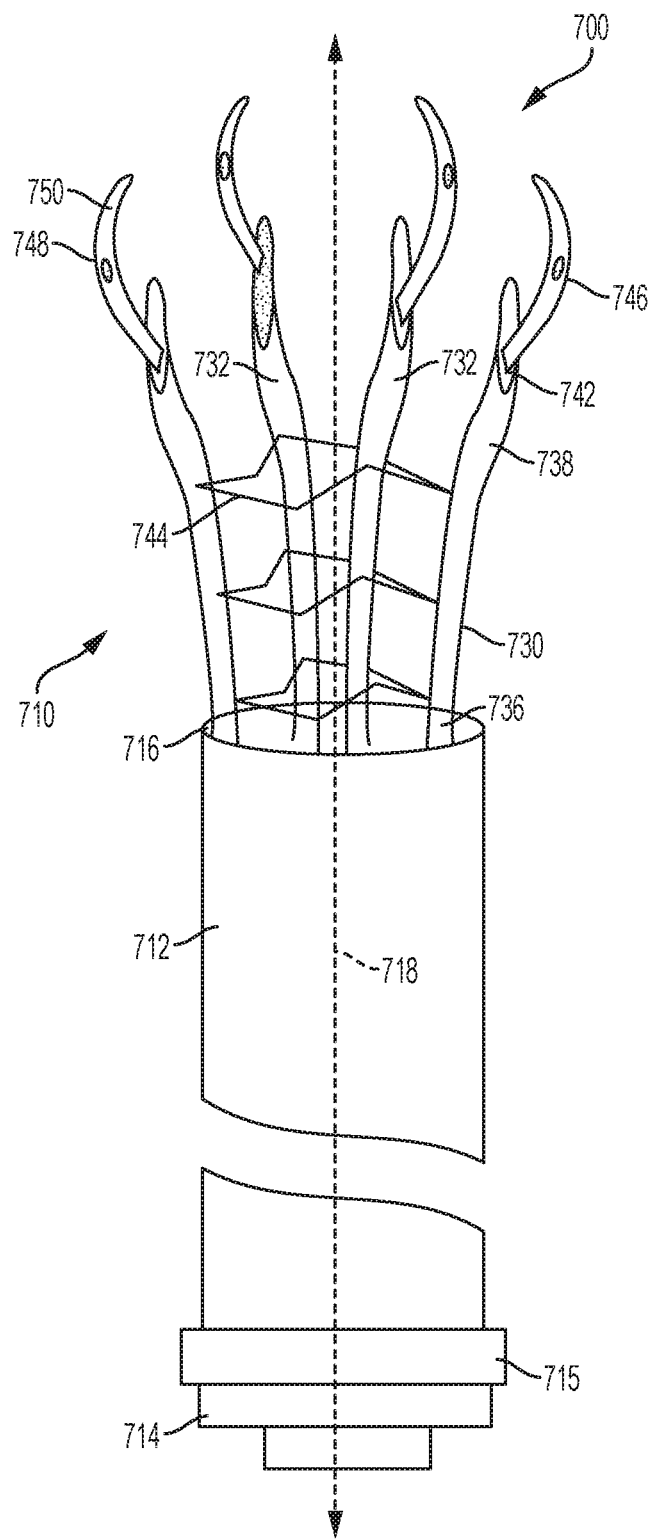
FIG. 1 shows a guide device, according to various examples.

The accompanying drawings are included to provide a further understanding of the disclosure and are incorporated in and constitute a part of this specification, illustrate embodiments, and together with the description serve to explain the principles of the disclosure.

DETAILED DESCRIPTION OF THE ILLUSTRATED EMBODIMENTS

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The instant disclosure generally relates to endoluminal and/or percutaneous access devices for accessing a target site within the body and directing a tool (e.g., a needle) to a desired position within the body in association with a medical procedure. Such procedures include any of a variety of treatments, such as surgical, diagnostic, palliative treatments, and others. Some examples relate to devices, systems and methods for guiding an endoluminal tool in a generally angularly offset direction relative to a longitudinal axis of the delivery system (e.g., perpendicular, radial, or askew directions). Such endoluminal tools can include endovascular tools (e.g., puncturing tools, delivery tools, or angioscopes) that are guided in a direction angularly offset, (e.g., askew or perpendicular) to a longitudinal axis of the delivery system. Such angular offsets can help assist with directing a tool toward or through a branch vessel, vessel wall, organ, a branch or wall of an endovascular device (e.g., a stent, graft, or stent graft), or other feature. For example, the endoluminal tool can be a puncturing tool for piercing, drilling, or cutting through a lumen wall and/or an angioscope for visualizing inside a lumen or across a lumen wall. In other examples, the endoluminal tool may include a delivery tool configured to deliver a therapeutic agent such as an occlusive material, a self-hardening gel, a self-expanding gel, or other suitable therapeutic agent to a location outside of the lumen wall. Various examples incorporate the ability to avoid occluding a lumen into which the delivery system is positioned and deployed (e.g., avoiding occlusion of blood flow in the case of endovascular applications).

As used herein, the terms "proximal" and "distal," in relation to a device or device component refer to directions closer to and farther away from the operator of the device respectively. As used herein, a vessel may be a blood vessel such as an artery, vein, capillary, or the like. In further examples, a vessel or bodily lumen may include an anatomical passageway such as an esophagus, urethra, stomach, intestine, or any other conduit or lumen existing in a body of a patient.

FIG. 1 shows a guide device 700 used to access the wall of a lumen, and provide access through the wall of the lumen from the inside of the lumen, according to some examples. As shown in FIG. 1, the guide device 700 includes an expandable portion 710 and a guide sheath 712. The expandable portion 710 may be configured to be received within the guide sheath 712 and to be movable relative to the guide sheath 712 along a central longitudinal axis 718 of the guide sheath 712.

In some examples, one or both of the expandable portion 710 or the guide sheath 712 comprise a material capable of detection from outside a patient's body. This material may be an integral part of expandable portion 710, guide sheath 712, or both, or may be a coating, or a separate marker connected thereto. Some example materials for ex vivo detection of the expandable portion 710 or the guide sheath 712 include radiopaque, echogenic, or magnetic materials. For example, the guide sheath 712 and/or the expandable portion 710 or other portions of the guide device 700 may include radiopaque or echogenic material to facilitate generally accurate positioning within the body of the patient using, for example, an X-ray or ultrasound machine.

As shown in FIG. 1, the guide sheath 712 has a proximal end 714, a distal end 716, and an inner diameter defining a guide lumen. The guide lumen is sized and shaped to allow the expandable portion 710 to be received within the guide sheath 812. The distal end 716 defines an opening into the guide lumen. The opening at the distal end 716 allows communication between the guide lumen and the outside of the guide sheath 712, for example to allow the expandable portion 710 to move between the outside of the guide sheath 712 and the inside of the guide sheath 712. The opening at the distal end 716 can be covered to close access to the guide lumen of the guide sheath 712, for example when the expandable portion 710 is received within the guide sheath 712.

In some examples, the guide sheath 712 is controllable and steerable from the proximal end 714 from a location external to a patient (e.g., using a control mechanism 715 illustrated generally in FIG. 1 as a knob or actuator that can be rotated to control angulation of the guide sheath 712). In various examples the guide sheath 712 has a length sufficient to extend from a target location inside the body of a patient to a location external to the body of the patient. For reference purposes, the guide sheath 712 is shown extending along the central longitudinal axis, and having an outer diameter defined in a transverse direction that is normal to the central longitudinal axis.

Materials used to construct the guide device 700, including the guide sheath 712, are generally biocompatible and facilitate delivery into the body. Such materials can include polymers, metals, or other materials as desired.

In some examples, the expandable portion 710 is configured to be controllable between a collapsed configuration within the guide sheath 712 (not shown) and an expanded configuration as shown. The expandable portion 710 may have an outer diameter defined as the widest distance between any two locations of the expandable portion 710 in the transverse direction. Although the term "diameter" is used with regard to the expandable portion 710, it should be understood that in addition to generally circular cross-sections, non-circular cross-sections (e.g., square or triangular) are contemplated and the term diameter is generally used to refer to the maximum outer dimension of the expandable portion 710. In general, the expandable portion 710 has an outer diameter, such as a first diameter, in the collapsed configuration that is less than an outer diameter, such as a second diameter, in the expanded configuration.

The expandable portion 710 is transitionable between a collapsed configuration and an expanded, or deployed configuration. The expandable portion 710 is generally insertable into the body of a patient in the collapsed configuration, in which the expandable portion 710 is received within, and has an outer diameter less than an inner diameter of the guide sheath 712. In some implementations, the expandable portion 710 is self-expanding as the expandable portion 710 is extended from the guide sheath 712, and self-collapsing when retracted into the guide sheath 712. The expandable portion 710 may be slidably received within the guide lumen defined by the inner diameter of the guide sheath 712 and extendable therefrom. The expandable portion 710 may be received within the guide sheath 712 such that the guide sheath 712 is an outer sheath positioned around the expandable portion 710 when the expandable portion 710 is in the collapsed configuration. In some examples, a handle, knob, or other control means (not shown) is grasped by a user (not shown) and actuated (e.g., slid longitudinally) to slide the expandable portion 710 into, and out of the guide sheath 712. In the collapsed configuration, the expandable portion 710 optionally has an outer diameter of 1-10 French or any value therebetween, although a variety of dimensions are contemplated.

The expandable portion 710 is configured to be controllable, or expandable, throughout a range of various degrees of expansion. In different terms, the expandable portion 710 is able to be controlled to various sizes. For example, the expandable portion 710 in its expanded configuration may have an outer diameter of about 1.0 mm, about 2.0 mm, about 3.0 mm, about 30 mm, about 45 mm, or about 65 mm, for example, although other values are also contemplated, including any of the ranges between the recited values.

As shown in FIG. 1, the expandable portion 710 includes a first arm 730 of a plurality of arms 732. Although multiple arms are shown in FIG. 1, examples with a single arm are also contemplated. The various arms 732 are optionally substantially similar, and thus description of the features of the first arm 730 will be understood to be applicable to the remaining arms 732 as well. For example, descriptions with reference to the first arm 730 are understood to apply to a single arm or more than one arm, such as two or more of the arms 732. The first arm 730 has an outer diameter, a first end portion 736 that is attached to the control mechanism 715 or other feature for actuating the arms 732, a second end portion 738, and a length defined between first and second end portions 736, 738. In some examples, one or more of the arms 732 has a shape memory or other bias that causes the arm(s) 732 to splay, or radially expand outwardly relative to the central longitudinal axis 718 during transition of the expandable portion 710 to the expanded configuration. For example, the second end portion 738 is configured to be expanded, or extend outwardly from the central longitudinal axis 718 to a greater extent than the first end portion 736.

In various examples, the arms 732 all have the same length. In some examples, one or more of the arms 732 have a length that is different than at least one of the remaining arms 732 (e.g., to access target sites at different positions along a body lumen). The first and second end portions 736, 738 of the first arm 730 and/or arms 732 correspond to the first and second ends of the expandable portion 710.

As shown in FIG. 1, the first arm 730 is shaped as a generally tubular structure with an inner diameter defining a lumen along the length of the first arm 730. For example, the first arm 730 may be a tube, such as a pipe or conduit, having a wall, extending the length of the first arm 730 from the first end portion 736 to the second end portion 738. The first arm 730 optionally has an inner surface at an inner diameter of the first arm 730 that defines a lumen along the length of the tube. In another example, the first arm 730 may include a filament (e.g., monofilament, wound or braided) or rod (e.g., monolithic), having a solid cross section along at least a portion of the length. For example, the first arm 730 may have a solid cross section along a first portion of the length and include a hollow cross-section along a second portion of the length (e.g., similar to that shown in FIG. 12B) that defines a lumen along the second portion.

In the expanded state as shown in FIG. 1, the first arm 730 is shaped to terminate and define a free end at the second end portion 738 at an oblique angle to the central longitudinal axis. That is, the second end portion 738 has a curve or bias in relation to the central longitudinal axis, and may include an angled termination (e.g., oblique) at the second end portion 738 resulting in the second end portion 738 opening at an angle (e.g., orthogonal angle) from the longitudinal axis. The curve or bias of the first arm 730 may be a smooth curve or may be angled or bent at an abrupt angle to the central longitudinal axis. The second end portion 738 of the first arm 730 may be sharpened (e.g., tissue penetrating) or may be generally rounded or dull (e.g., atraumatic). For example, the second end portion 738 can define a tine or pointed tip suitable for insertion or cutting into tissue (e.g., vascular tissue). The second end portion 738 may include an angular taper, for example at a slant or diagonal from the length of the first arm 730.

As shown, the arms 732 are connected to each other with one or more control connections 744. The control connections 744 may be configured to define (e.g., limit) a distance between the arms 732 and/or a position of the arms 732 in relation to each other. The control connections 744 are elongate members such as one or more strands or fibers that extend between, and connect, adjacent arms 732 to limit the extent to which the arms 732 splay, radiate, or otherwise expand outward relative to one another. In some examples, the control connections 744 have a shape memory for elastically transitioning between the collapsed and expanded configurations. In some embodiments, the control connections 744 self-deploy (e.g., spring outwardly) to a suitable position when the expandable portion 710 is in the expanded configuration and help to position and limit the arms 732 at a predetermined distance and orientation relative to one another.

The expandable portion 710 is sized, shaped, and otherwise configured such that at least some fluid flow is maintained through a vessel when the expandable portion 710 is inserted within the vessel (e.g., there is only minor disruption to flow through the vessel), while expandable portion 710 is in the expanded position, and/or during the transition to the expanded position. For instance, the guide device 700 has gaps between the arms 732 and the guide sheath 712, and the expandable portion 710 has gaps between individual arms 732 when the expandable portion 710 is in the expanded configuration and during the transition between the collapsed configuration and the expanded configuration.

In some embodiments, if a single arm such as the first arm 730 is included in the expandable portion 710, liquids (e.g., blood) and/or gases (e.g., air) are able to flow past the single arm to help avoid impeding the flow of bodily fluids, for example. In examples having two or more arms 732, in the expanded configuration, the arms 732 are spaced apart from each other and define spaces between the arms 732 through which fluid can pass. In this manner, the arms 732 are configured to facilitate continuous fluid flow, such as aortic downstream perfusion, throughout the deployment of the guide device 700 and throughout the transition between the collapsed configuration and the expanded configuration.

As shown in the expanded configuration or expanded state in FIG. 1, the first arm 730 includes an aperture 742 at the second end portion 738. The aperture 742 is positioned at the end of the first arm 730 and/or along the side of the first arm 730 and is oriented to face radially outward (e.g., substantially orthogonal) relative to the central longitudinal axis. As shown, the aperture 742 is a hole through the wall of the first arm 730, from inside the first arm 730 to the outside of the first arm 730. In the examples shown in FIGS. 1 to 5, the aperture 740 into the first arm 730 is formed by cutting an end of the first arm 730 (e.g., at an angle, resulting in an angled opening), to form an exit from the inner lumen of the first arm 730. The aperture 740 is in communication with the inner lumen of the first arm 730 and a guide path is defined from the inner lumen of the first arm 730, through the aperture 742, to the outside of the first arm 730. As the arms 732 expand outwardly, to the deployed configuration, the opening, or exit is positioned at an angle relative to the central longitudinal axis of the guide device 700. In at least this manner, a tool (e.g., needle), or multiple tools, can be extended from the arms 732 at desired angles relative to the central longitudinal axis of the guide device 700.

In some examples, the expandable portion 710 is configured to self-expand upon release from a constraining mechanism such as the guide sheath 712 (e.g., upon being longitudinally displaced from the guide sheath 712). For example, the expandable portion 710 can be fabricated from alloys, shape-memory alloys, or polymers such as stainless steel, nitinol, polyurethanes, or the like such that it is configured to self-expand to the deployed configuration. In some embodiments, various portions of the guide device 700 are formed from shape memory alloys that provide a suitable pre-shaped bias, such as a curve having a suitable radius, upon deployment. Example shape-memory alloys that may be used include NiTi, AgCd, AuCd, CuAlNi, CuSn, CuZn, FePt, MnCu, FeMnSi, CoNiAl, CoNiGa, NiFeGa, TiNb, NiTiHf, NiTiPd, or NiMnGa. Although self-expanding, or biased structures are described, it should be understood that expandable structures (e.g., balloon expandable) are also contemplated.

In some examples, the plurality of arms 732, including the first arm 730, is biased to assume a suitable predetermined shape when in the expanded configuration. In some examples, the second end portion 738 of the first arm 730 has a shape memory or other bias to direct the aperture 742 in a suitable direction when the expandable portion 710 is transitioned to the expanded state. For example, the second end portion 738 of the first arm 730 is curved or biased and the aperture 742 is located at a suitable location along the curve to achieve the desired angle for the aperture 742. In some examples, the aperture 742 of the first arm 730 is at an outermost radial portion of the curve (e.g., at the end of the first arm 730 as shown in FIG. 1) such that the aperture 742 faces radially outward (e.g., substantially perpendicular to the central longitudinal axis of the expandable portion 710). Additionally, or alternatively, the first arm 730 has the aperture 742 located at a forward facing radial position such that following expansion, the aperture 742 is angled from the central longitudinal axis of the expandable portion 710. The aperture 742 may be positioned to face at any desired angle from the central longitudinal axis 718 of the of the guide device 700.

As shown in FIG. 1, the guide device 700 is optionally utilized to deploy an endoluminal tool 746. The endoluminal tool 746 is part of the guide device 700 and provides additional features that allow a user to access a desired location within a lumen of a vessel. In some examples, the endoluminal tool 746 is deployed from within the first arm 730, where the first arm 730 directs the endoluminal tool 746 toward a desired contact site within a lumen. That is, the endoluminal tool 746 is optionally slid longitudinally within the first arm 730, the endoluminal tool 746 extends from the arm, and as the endoluminal tool 746 extends from the first arm 730 the first arm 730 guides the endoluminal tool 746 away from the expandable portion 710 and controls the angle that the endoluminal tool 746 extends relative to the central longitudinal axis of the guide device 700.

The endoluminal tool 746 is any tool suitable for deployment and/or use within a lumen of a body of a patient and/or an implanted medical device (e.g., a stent, graft, or stent graft), for example. The endoluminal tool 746 may be an angioscope, an ablation device, a puncturing tool, a piercing catheter, a re-entry device, a stent, a stent graft, a drug delivery tool, an occlusion tool, or any of a variety of tools. In a further example, the endoluminal tool 746 may be a needle, such as a hollow needle, or needles, such as microneedles. The endoluminal tool 746 may include a device for piercing, drilling, or cutting a lumen from the inside. For example, the endoluminal tool 746 may include an end effector 748 that includes a pointed tip 750.

The endoluminal tool 746 may have a pre-shaped curve and/or include a shape memory. As an example, an endoluminal tool 746 having a preshaped curve can be deployed from the first arm 730 and contact a lumen wall such as a wall of a vein, artery, or stent at an angle from the central longitudinal axis of the guide device 700. The endoluminal tool 746 can be controlled to contact the lumen wall at a suitable angle and, in some examples, penetrates the lumen wall. Examples of an endoluminal tool 746 that are configured to access a lumen wall include tools that can penetrate the wall of a vessel at a controllable angle and provide a user, such as a healthcare worker, with access across the wall of the vessel. In some instances, the endoluminal tool 746 can provide access to the inner surface of the vessel from inside of the vessel. The endoluminal tool 746 can also provide access through the wall of the vessel. For example, the endoluminal tool 746 can provide access to the outer surface of the vessel from inside the vessel, and/or access to the inside of a vessel from outside the vessel. In some examples, the endoluminal tool 746 can access the outer and/or inner surface of a second vessel from a starting location that is within a first vessel. For example, the endoluminal tool 746 can be deployed from inside a first vessel that is adjacent to the second vessel, and the endoluminal tool 746 can access the outer or inner surface of the second vessel while the first arm 730 is inside the first vessel. The endoluminal tool 746 may be a transvascular tool (i.e. a tool that is capable of accessing across the wall of a blood vessel or similar vessel, such as controllably accessing a location outside a vessel from a starting location that is within the vessel).

In some examples, the endoluminal tool 746 may be a transvascular tool that is configured to deliver a therapeutic agent to a location outside of the lumen wall as shown and discussed in further detail with reference to FIGS. 16-17. The therapeutic agent may be, for example, an occlusive material, a self-hardening and/or self-expanding gel, or other similar material capable of modifying and/or stabilizing the anatomy of the lumen. For example, the therapeutic agent may impart a pressure on an abluminal surface of the vessel, thereby pushing the lumen wall inward and reducing the diameter of the vessel or, in some instances, occluding the vessel entirely. In other examples, the therapeutic agent may substantially surround the abluminal surface of the vessel to prevent expansion of the vessel such as in the case of an aneurysm. Use of such therapeutic agents may eliminate the need for placement of other occlusion devices or endoluminal devices (i.e., stents, grafts, stent-grafts, occluders, and other devices) within the interior of the vessel, which may reduce the risk of certain undesirable side-effects such as stenosis and accidental migration of the device downstream.

In some examples, the first arm 730 houses the endoluminal tool 746 and directs the endoluminal tool 746 using the curve or bias of the first arm 730. The aperture 742 may also be configured to direct the endoluminal tool 746 at a suitable angle relative to the first arm 730. For example, the size and shape of the aperture 742 may also assist in directing the endoluminal tool 746 as desired. In various examples, the endoluminal tool 746 may be positioned to face at an angle of about 10°, 20°, or 30°, or about 45°, 60°, or 90°, or any angle between the foregoing values from the central longitudinal axis of the expandable portion 710, although other values are also contemplated.

In some examples, more than one of the plurality of the arms 732 contains an endoluminal tool, such as the endoluminal tool 746. In examples having more than one endoluminal tool 746, each endoluminal tool 746 may be the same, or one or more arms 732 may include an endoluminal tool 746 that is different than an endoluminal tool 746 in another one of the arms 732.

FIGS. 2 to 5 show the guide device 700 at various stages of deployment, according to some methods of use. Some deployment processes include deploying the guide device 700 through a lumen 760 of a vessel 762 to a treatment site, outwardly extending or expanding the expandable portion 710, and directing an endoluminal tool 746 (e.g., an endovascular tool for puncture or cannulation) to access a target site with the guide device 700. In some examples, the guide device 700 is inserted to a desired location within the patient's anatomy using fluoroscopy, ultrasound, or other imaging/detection techniques. The guide device 700 provides an endoluminal access device which allows a user to access a target side inside the lumen of a body from a remote location, such as outside of the body, with minimal trauma to the lumen proximate the target site.

Figure 2:
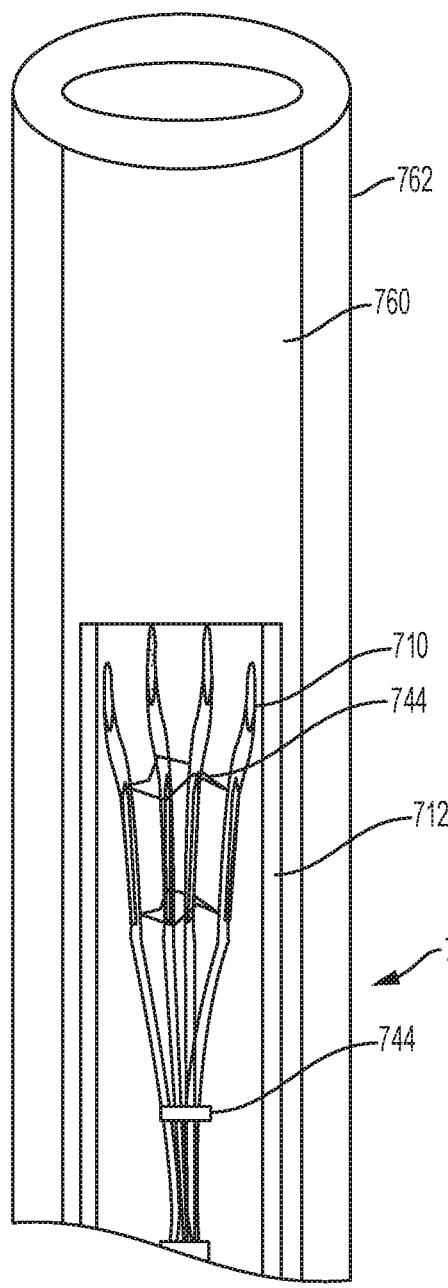
FIG. 2 shows a deployment procedure for using the guide device of FIG. 1, according to various examples.

As shown in FIG. 2, the guide device 700 is inserted into the lumen 760 of the vessel 762. Inserting the guide device 700 through the lumen 760 of the vessel 762 includes deploying the guide device 700 from an access location remote from the treatment site and advancing the guide device 700 through the vessel 762 until the guide device 700 reaches a suitable treatment site. In at least this manner, the guide device 700 is deliverable to a desired site in a body by following a transluminal path. As shown, in some deployment processes, the expandable portion 710 is positioned within the guide sheath 712 as the guide device is advanced through the vessel 762. The guide device 700 is inserted and advanced through the lumen 760 of the vessel 762 by controlling the guide device 700 from outside the body of the patient, such as by manipulating the control mechanism 715 and/or the proximal end 714 of the guide sheath 712 shown in FIG. 1.

The guide device 700 can be positioned within the vessel 762 and located at the treatment site with the use of visualization techniques such as fluoroscopic and/or ultrasonic imaging, located outside the body of the patient. With the guide device 700 in position at the treatment site, the expandable portion 710 can be deployed from the guide sheath 712. The expandable portion 710 is moved between the collapsed configuration and the expanded configuration by manipulating the proximal end 714 of the guide sheath 712, for example, and the expandable portion 710 from a location external to a patient (e.g., by manipulating the control mechanism 715).

As shown in FIG. 2, the guide device 700 allows continuous fluid flow through the vessel 762, such as aortic downstream perfusion, throughout deployment of the guide device 700 and operation of the endoluminal tool 746. That is, the guide device 700 does not occlude the vessel 762, but allows at least some fluid flow through the vessel 762 (e.g., around the guide sheath 712 and past/through the expandable portion 710) when the guide device is being inserted through the vessel, when the guide device 700 is in the collapsed configuration, and/or when the guide device 700 is moved between the collapsed configuration and the expanded configuration.

Figure 3:
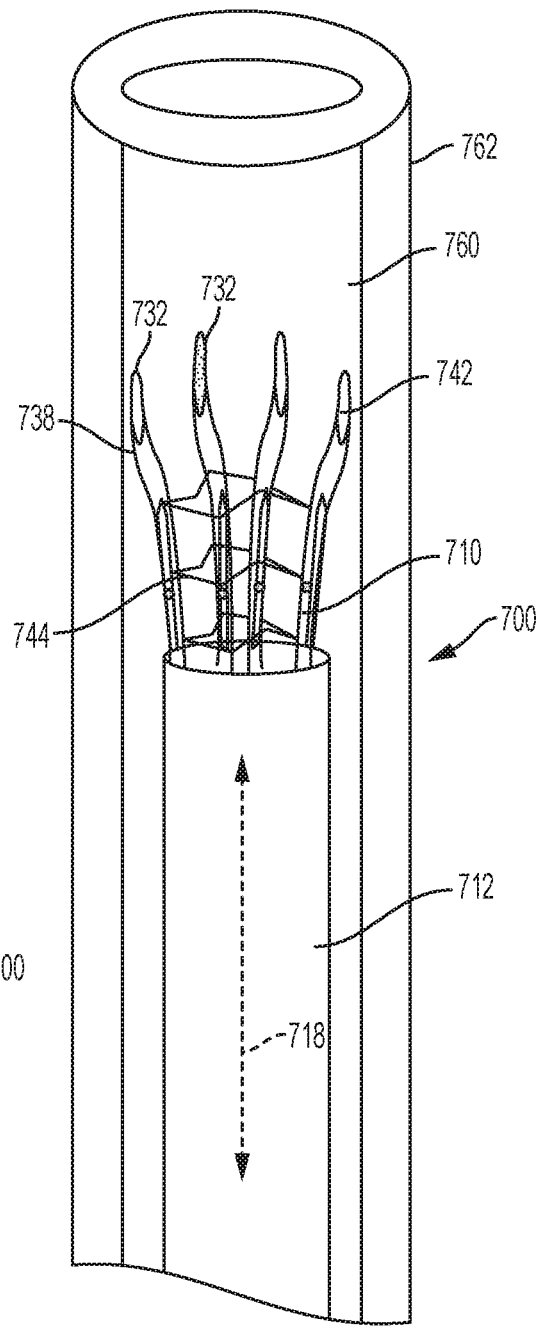
FIG. 3 shows a deployment procedure for using the guide device of FIG. 1, according to various examples.

As shown in FIG. 3, after the guide device 700 has reached a suitable position, the expandable portion 710 is deployed. The expandable portion 710 is deployable by holding the guide sheath 712 stationary while the expandable portion 710 is moved longitudinally in relation to the guide sheath 712, according to some examples. Alternatively, the guide sheath 712 may be moved longitudinally while the expandable portion 710 is held stationary. Moving the expandable portion 710 along the central longitudinal axis 718, deploys the second end portions 738 of the arms 732 out of the guide sheath 712. Moving the expandable portion 710 relative to guide sheath 712 along the central longitudinal axis also causes the expandable portion 710 to extend or expand outward from the central longitudinal axis. The extent to which the expandable portion 710 expands can be controlled by one or more control connections 744. The extent to which the expandable portion 710 expands can also be controlled by controlling how much the expandable portion 710 is moved relative to the guide sheath 712 along the central longitudinal axis. That is, the outer diameter of the expandable portion 710 in the expanded configuration may be controlled by advancing the arms 732 further out of the guide sheath 712, which results in the arms 732 further expanding.

In some deployment processes, the expandable portion 710 is expanded until the arms 732 reach a predetermined expansion limit and/or confront a barrier outside the expandable portion 710, such as an inner surface of the lumen 760 into which the guide device 700 is positioned. The expandable portion 710 is expanded until the second end portion 738 of each of the arms 732 is adjacent to or confronts a surface of the lumen 760 of the vessel 762. That is, the expandable portion 710 is controllable to expand until the arms 732 are proximate to but not touching the surface of the lumen 760. The expandable portion 710 is also controllable to expand until it comes in contact with or presses against the surface of the lumen 760. The expandable portion 710 may be controlled such that each of the arms 732 expands symmetrically about the central longitudinal axis. The expandable portion 710 can be controlled such that in the expanded configuration, each of the arms 732 are an equal distance away from, or pressing with an equal force against, the surface of the lumen 760. The expandable portion 710 is expanded until the aperture 742 is at a suitable distance from, and/or at a suitable angle to, the surface of the lumen 760.

Figure 4:
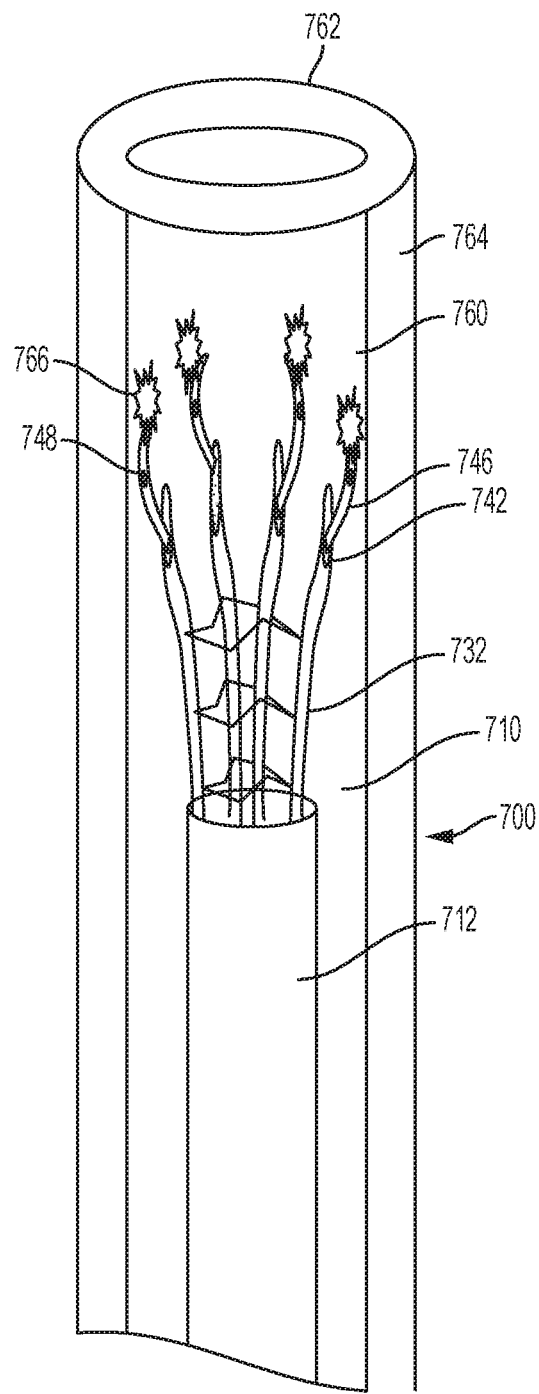
FIG. 4 shows a deployment procedure for using the guide device of FIG. 1, according to various examples.

As shown in FIG. 4, with the expandable portion 710 deployed to an expanded configuration with the first arm 730, or arms 732 expanded to a suitable outer diameter, the endoluminal tool 746, or tools are deployed, or extended. By way of example with reference to the first arm 730, the endoluminal tool 746 is deployed by extending the endoluminal tool 746 through the first arm 730. When the endoluminal tool 746 is deployed, the first arm 730 biases the endoluminal tool 746 at a suitable angle relative to the central longitudinal axis of the expandable portion 710. For example, the first arm 730 and the aperture 742 define a delivery angle relative to the central longitudinal axis of the guide device 700 and or expandable portion 810, and the endoluminal tool 746 is deployed at the delivery angle outward from the expandable portion 710. The expandable portion 710 provides a guide assembly such that the endoluminal tool 746 is delivered at an acute angle relative to the central longitudinal axis of the guide device 700. In some examples, the guide sheath 712 and the expandable portion 710 are held stationary while the endoluminal tool 746 is deployed through, or otherwise moved relative to the first arm 730 and through aperture 742.

As shown in FIG. 4, in some examples the endoluminal tool 746 is used to access the wall 764 of the vessel 762. In some methods, the endoluminal tool 746 is used to provide a treatment such as delivering a therapeutic agent or conducting a therapy to the vessel 762 or to the space outside of the vessel 762 (e.g., the perivascular space). If desired, the endoluminal tool 746 can include an end effector 748 that is manipulated (e.g. extended from the aperture 742) such that an electrode or other end effector 748 is usable to drill, pierce, or cut into or completely through the wall 764 of the vessel 762. In some examples, the end effector 748 is usable to form an access point 766 into or entirely through the wall 764 of the vessel 762 to the outside of the vessel 762. In some examples, the end effector 748 can be used to place an anchor into the wall 764 of the vessel 762.

In some examples, the endoluminal tool 746 includes a needle, for example a hollow needle or a needle suitable for delivering a suture. The expandable portion 710 deploys the needle at a delivery angle relative to the central longitudinal axis of the expandable portion 710, and biases the hollow needle against the wall 764 of the vessel 762. The expandable portion 710 directs the needle at a delivery angle outward from the expandable portion 710 and toward the wall 764 of the vessel 762. The needle is used to penetrate the wall 764 of the vessel 762 at a suitable angle at the access point 766. The needle is used, for example, to place a suture in the wall 764 of the vessel 762, or to deliver a medication, such as with a hollow needle, or to form a fenestration through the wall of the vessel or organ, for example. As discussed above, the needle can also be used to deliver a therapeutic agent to an abluminal surface of the vessel.

In another embodiment, the endoluminal tool 746 includes a puncture tool for entering and piercing an endoluminal device (e.g., a stent graft) from within the endoluminal device to form an opening through the endoluminal device at a desired location (e.g., at a location corresponding to a branch vessel). In other embodiments, the endoluminal tool 746 is used to fenestrate an endoluminal device (e.g., a stent graft) from outside the endoluminal device.

Figure 5:
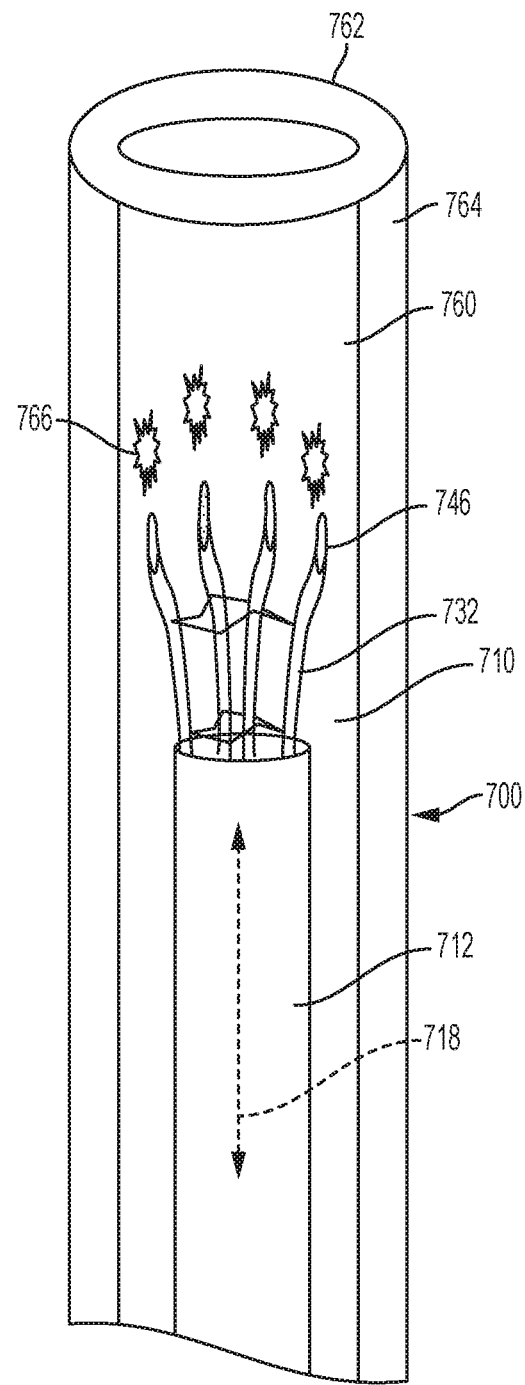
FIG. 5 shows a deployment procedure for using the guide device of FIG. 1, according to various examples.

As shown in FIG. 5, the endoluminal tool 746 is removable from a treatment site following a suitable therapy. The endoluminal tool 746 may be sized and shaped such the endoluminal tool 746 is better able to be advanced and retracted into and from the access point 766 with minimal trauma to the vessel 762. The endoluminal tool 746 is removed from the wall 764 of the vessel 762 and retracted into the expandable portion 710. The endoluminal tool 746 may be retracted into the expandable portion 710 by slidably receiving the endoluminal tool 746 into one of the arms 732. In some examples, the expandable portion 710 is then collapsed and transitioned to deflect inwardly (e.g., by withdrawing the expandable portion into the guide sheath 712). With the expandable portion 710 retracted into the guide sheath 712, the guide device 700 is removed from the vessel 762.

The foregoing examples provide for various features and advantages, including that guide device 700 is endoluminally deployable through bodily vessels, including blood vessels or other bodily lumens such as the urethra or esophagus of a patient. The guide device 700 can help an operator access the wall of the vessel for a deployment of a tool at a desired orientation, or angle of approach, at the target site. For example, the guide device 700 can provide directional control of an endoluminal tool 746 along an inner surface of the vessel, such as along the surface of a lumen defined by the vessel. The guide device 700 can deploy an endoluminal tool to a treatment site and direct or bias an endoluminal tool in a direction generally at an angle or off axis to the central longitudinal axis of the guide device and/or the vessel.

Figure 6:
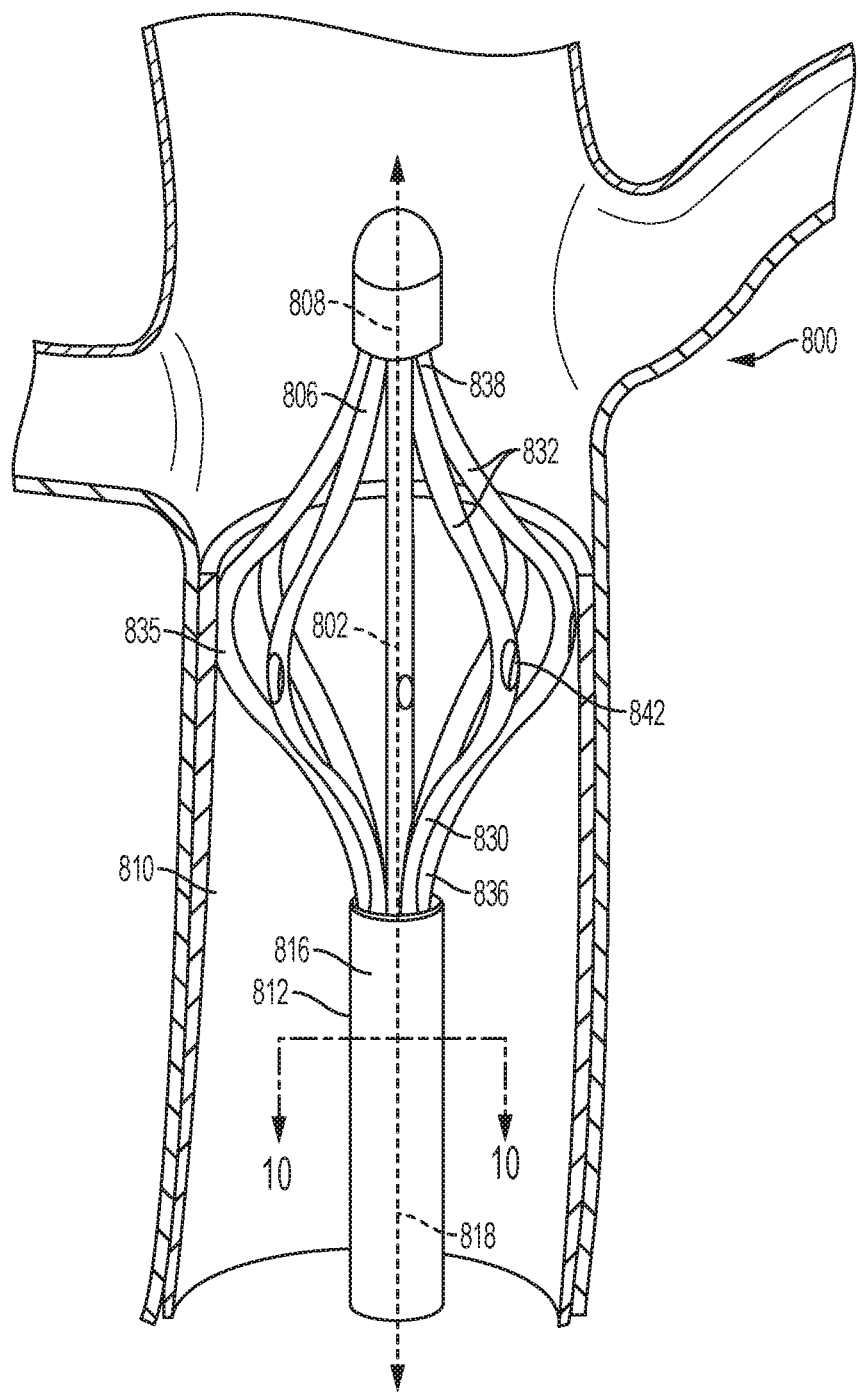
FIG. 6 shows another guide device, according to various examples.

FIG. 6 shows another guide device 800, according to some examples. As shown, the guide device 800 includes an inner shaft 802, an expandable portion 810, and a guide sheath 812. For reference, FIG. 6 shows the expandable portion 810 in a deployed, or expanded configuration. The inner shaft 802 and the expandable portion 810 are received within the guide sheath 812 and, in some examples, are movable longitudinally relative to guide sheath 812 along the central longitudinal axis 818 of the guide device 800. Although not required, as shown, the guide device 800, the inner shaft 802, the expandable portion 810, and the guide sheath 812 can share a common, central longitudinal axis 818.

FIG. 6 shows a distal portion of the guide device 800, which includes the expandable portion 810 and the guide sheath 812. The guide device 800 is typically provided with a desired length so that the distal portion of the guide device 800 is locatable within a body of a patient while a proximal portion (not shown) of the guide device 800 is external to the patient and able to be manipulated by a user (e.g., to locate the distal portion of the guide device 800 as desired and to actuate the expandable portion 810 between expanded and collapsed configurations).

As shown in FIG. 6, the guide sheath 812 is an elongated tube and extends from a proximal portion (not shown) to a distal end 816 and has an inner diameter that defines a guide lumen, with the distal end 816 defining an opening into the guide lumen. In some examples, the guide sheath 812 is controllable and steerable from the proximal portion of the guide device 800 such as by using a control mechanism (e.g., using steering wires or other steering mechanisms). In some examples, the guide sheath 812 has a length sufficient to extend from a target location inside the body of a patient to a location external to the body of the patient.

As shown in FIG. 6, the inner shaft 802 has a proximal portion (not shown), and a distal end 806. Although not required, as shown, the inner shaft includes a tip 808 attached to the distal end 806. The inner shaft 802 is receivable within the guide sheath 812. The inner shaft 802 may be slidably received within the guide sheath 812, where the inner shaft 802 is movable between a first position in which the distal end 806 of the inner shaft 802 is farther from the distal end 816 of the guide sheath 812, and a second position in which the distal end 806 of the inner shaft 802 is closer to the distal end 816 of the guide sheath 812.

As shown in FIG. 6, the expandable portion 810 includes at least a first arm 830. In some embodiments, the expandable portion 810 may include two or more arms 832. The various arms 832 are optionally substantially similar, and thus description of the features of the first arm 830 of the plurality of arms 832 will be understood to be applicable to the remaining arms 832 as well. The first arm 830 has a first end portion 836, a second end portion 838, and an intermediate portion 835 between the first and second end portions 836, 838. In some instances, the first and second end portions 836, 838 of the first arm 830 define the first and second ends of the expandable portion 810. As shown in FIG. 6, the second end portion 838 of the first arm 830 is located distal to the first end portion 836 and the intermediate portion 835, and is connected to the tip 808. In examples of the expandable portion 810 having multiple arms, the tip 808 keeps the second end portion 838 of the arms 832 together. The first arm 830 may have any cross-sectional shape including circular, oval, triangular, square, polygon shaped or combinations thereof.

The expandable portion 810 comprises a radially expandable structure that is moveable between a collapsed position and an expanded position. The expandable portion 810 has an outer diameter defined as the widest distance between any two locations on the expandable portion 810 in the radial direction (e.g. transverse to the central longitudinal direction). For example, the outer diameter of the expandable portion 810 may be the greatest distance between two points in the radial direction. Although the term "diameter" is used with regard to the expandable portion 810, it should be understood that in addition to generally circular cross-sections, non-circular cross-sections (e.g., square or triangular) are contemplated and the term diameter is generally used to refer to the maximum outer dimension of the expandable portion 810. In general, the expandable portion 810 has an outer diameter in the collapsed configuration that is less than an outer diameter in the expanded configuration.

The expandable portion 810 is configured to be controllable throughout a range of various degrees of expansion such that the outer diameter is controllable to various sizes, or diameters. For example, the expandable portion 810 in its expanded position may have an outer diameter as small as about 1.0 mm, about 2.0 mm, or about 3.0 mm, or as large as about 30 mm, about 45 mm, or about 65 mm, for example, and any value in between, although other values are also contemplated.

The expandable portion 810 is controllable to a collapsed configuration with an outer diameter less than the inner diameter of the guide sheath 812. The expandable portion 810 is configured to be movable relative to the guide sheath 812 along the central longitudinal axis. The expandable portion 810 may be received within the guide sheath 812, for example, by advancing the distal end 816 of the guide sheath 812 over the expandable portion 810. That is, in the collapsed configuration the expandable portion 810 is slidably received within the guide sheath 812 and extendable therefrom. In some implementations, the expandable portion 810 is self-expanding as the expandable portion 810 is extended from the guide sheath 812, and self-collapsing when retracted into the guide sheath 812.

The expandable portion 810 is structurally or materially configured such that at least some continuous flow is maintained through a vessel with the guide device 800 positioned within the vessel (e.g., with only minor disruption to flow). The arms 832 may separate from each other, creating space between the arms 832 as the expandable portion 810 outwardly extends. The arms 832 may be formed to define an open interior structure bounded by a mesh like structure or a ribbed structure, for example. The spaces between the arms 832 may be generally longitudinally oriented (e.g., along the central longitudinal axis 818 or have other configurations (e.g., diagonal, helical, or others).

As shown in FIG. 6, in the expanded configuration the arms 832 are spaced apart to define spaces between the arms 832 such that fluid is allowed to flow around the guide sheath 812 and through the spaces between the arms 832. The expandable portion 810 has gaps between individual arms 832 and defines a plurality of open spaces between individual arms 832 and an open interior space through which fluid can flow when the expandable portion 810 is in the expanded configuration. In the expanded configuration, the expandable portion 810 also has gaps between the arms 832 and the inner shaft 802 through which fluid can flow when the expandable portion 810 is in the expanded configuration. In some examples, fluid can also flow through the spaces between the arms 832 when the expandable portion 810 is being transitioned between the collapsed configuration and the expanded configuration.

Among other advantages, continuous perfusion of downstream body systems can also be beneficial. As another example, maintaining downstream perfusion can help allow for positional accuracy of the guide device 800 during a procedure within a vessel, because allowing continuous fluid flow reduces the need to withstand or resist pressures associated with temporary occlusion of the vessel. In other contexts, it may be desirable to block, or partially block fluid flow when the guide device 800 is deployed to the expanded state. In such instances, the arms 832 may include membranes (e.g., occluding or filtering) extending between the arms 832 to block the spaces.

As shown in FIG. 6, the first arm 830 includes an aperture 842. The aperture 842 is positioned along the side of the first arm 830, at the intermediate portion 835 and is directed in a generally radial direction. In some configurations, the first arm 830 is generally tubular, including a wall that extends along the length of the first arm 830 and defines an inner lumen. As shown, the aperture 842 is a hole through the wall and serves as a portal, or opening into the inner lumen of the first arm 830. In embodiments where the first arm 830 has a solid cross section along a first portion of the length, the aperture 842 may be a hole through the wall of the section of tube that forms a second end portion of the first arm 830. As the arms 832 expand outwardly, to the deployed or expanded configuration, the aperture 842 is positioned at an angle relative to the central longitudinal axis of the guide device 800. In at least this manner, a tool 843 (e.g., a needle), or multiple tools, can be extended from the arms 832 at desired angles relative to the central longitudinal axis of the guide device 800. For example, as discussed above, the tool 843 may be a transvascular tool capable of piercing the lumen wall and/or a needle or hollow needle capable of delivering a therapeutic agent to an abluminal surface of the lumen wall. In certain instances, the tool 843 may include both a transvascular tool and a needle such that the agent may be delivered through the needle once the lumen wall has been pierced.

The guide device 800 may comprise any configuration or materials that facilitate the expandable portion 810 moving between its collapsed position and its outwardly extending expanded position. The guide device 800 may be characterized by varying degrees of rigidity or softness, which may further vary along the length. The guide device 800 may be flexible, e.g. when required to traverse through tortuous vasculature. The expandable portion 810 may comprise a flexible material that is sufficiently rigid and strong to outwardly extend and maintain its expanded position during a procedure. The expandable portion 810 may comprise a material that is sufficiently resilient to support a vessel wall during a procedure, such as a fenestration procedure. The expandable portion 810 may be comprised of a biocompatible material, including nitinol, silicon, latex, polyurethane, polyvinyl chloride, polysiloxanes, polycarbonate, polyethylene, nylon, PTFEs (e.g., ePTFEs), stainless steel, or any combination thereof. The expandable portion 810, or any portion thereof, can be hydrophilic or hydrophobic as desired.

The expandable portion 810 may be made to self-expand upon release from a constraining mechanism such as the guide sheath 812. The expandable portion 810 may be fabricated from shape-memory alloys or polymers such as stainless steel (SST), nitinol, polyurethanes, or the like. In some embodiments, various portions of the guide device 800 are formed from shape memory alloys that provide a suitable preshaped bias, such as a curve having a suitable radius, upon deployment. Example shape-memory alloys that may be used include NiTi, AgCd, AuCd, CuAlNi, CuSn, CuZn, FePt, MnCu, FeMnSi, CoNiAl, CoNiGa, NiFeGa, TiNb, NiTiHf, NiTiPd, or NiMnGa.

One or both of the expandable portion 810 or the guide sheath 812 may comprise a material capable of detection, such as from outside a patient's body. This material may be an integral part of the expandable portion 810, the guide sheath 812 or both, or may be a coating, or a separate marker connected thereto. Some example materials for ex vivo detection of the expandable portion 810 or the guide sheath 812 include radiopaque, echogenic, or magnetic materials. The guide sheath 812 and/or the expandable portion 810 or other portions of the guide device 800 may include radiopaque or echogenic material to facilitate generally accurate positioning within the body of the patient using, for example using an X-ray or ultrasound machine.

FIGS. 7A to 7C, 8A to 8C, and 9A to 9C show the guide device 800 at various stages of deployment, according to some methods of use. Some deployment processes include deploying the guide device 800 through the anatomy of a patient, such as through a lumen of a vessel to a treatment site. The deployment process includes outwardly extending or expanding the expandable portion 810 at an angularly offset direction relative to the central longitudinal axis, and directing an endoluminal tool 846 (e.g., an endovascular tool for puncture or cannulation) to the selected target site with the guide device 800. In some examples, the guide device 800 is positioned to a desired location within the anatomy using fluoroscopy, ultrasound, or other imaging/detection techniques. The guide device 800 may be positioned within a vessel using visualization techniques such as those previously described. Once the guide device 800 is in a suitable position, the endoluminal tool 846 is deployed through the guide device 800 to the selected treatment site. As disclosed below, expanding or collapsing the expandable portion 810 is performed by selective axial displacement of the expandable portion 810 and the inner shaft 802 and/or guide sheath 812 to one another.

Figure 7A:
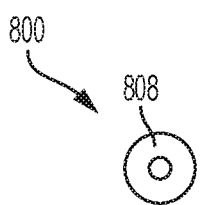
FIGS. 7A to 7C show front, side, and isometric views the guide device of FIG. 6, where the guide device is shown in an undeployed configuration, according to various examples.
Figure 7B:
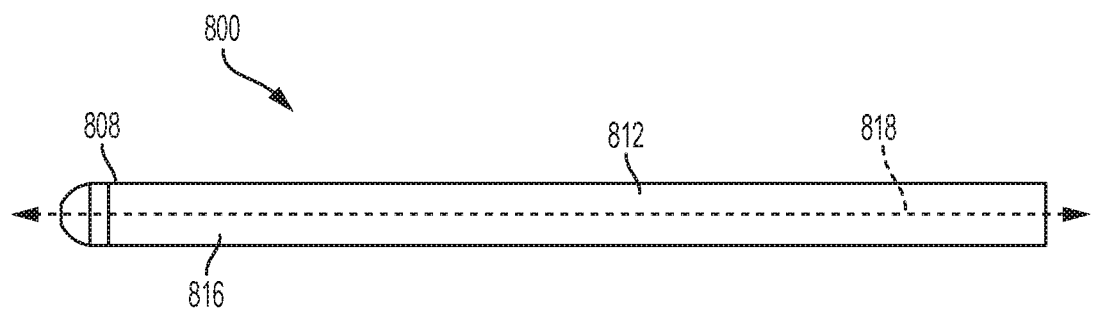
Figure 7C:
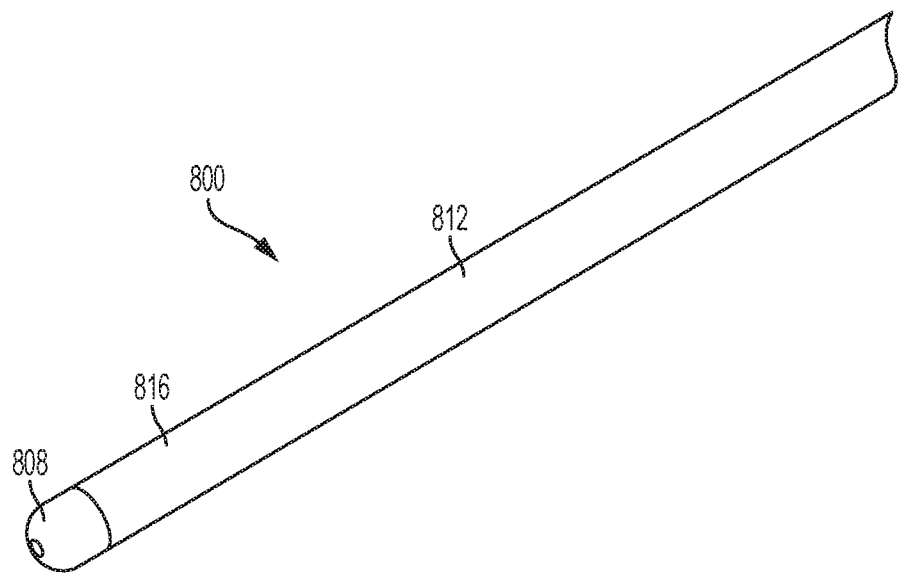

FIGS. 7A to 7C, show the guide device 800 in a collapsed configuration, from end, side, and isometric views, respectively, according to some examples. As shown in FIGS. 7A to 7C, when the guide device 800 is in a collapsed configuration the guide sheath 812 and the tip 808 are visible. That is, the expandable portion 810 is covered by the guide sheath 812 when the guide device 800 is in the collapsed configuration. With the guide device 800 in the collapsed configuration, the guide device 800 may be inserted into a lumen, for example a lumen of a vessel of a patient's anatomy. The guide device 800 may be maintained in the collapsed configuration by coupling or attaching the distal end 816 of the guide sheath 812 to the tip 808 to define a smooth, atraumatic, and diametrically constant outer profile that is resistant to fluid ingress, for example. That is, the tip 808 and the guide sheath 812 in combination form a continuous body having a continuous outer surface around the expandable portion 810 and encase the expandable portion 810 as the guide device 800 is deployed through a vessel to a treatment site. Having a continuous outer surface may ease the insertion of the guide device 800. For example, the continuous outer surface may help inhibit the expandable portion 810 from rubbing the surface of the lumen of the vessel during insertion. The guide device 800 may be inserted and advanced through the lumen of the vessel, and positioned within the vessel and located at the treatment site with the use of a detector, such as fluoroscopic and/or ultrasonic imaging, located outside the body of the patient.

Figure 8A:
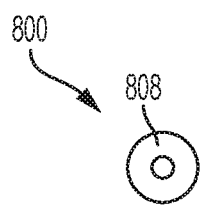
FIGS. 8A to 8C show the guide device of FIGS. 7A to 7C from front, side, and isometric views, where the guide device is shown in an intermediate deployment configuration, according to various examples.
Figure 8B:
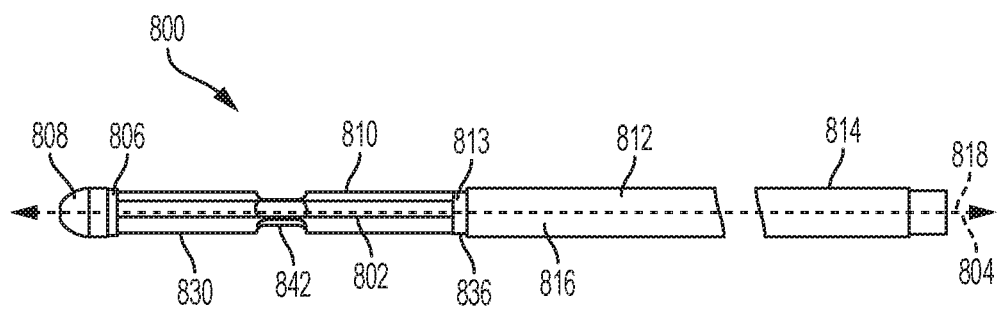
Figure 8C:
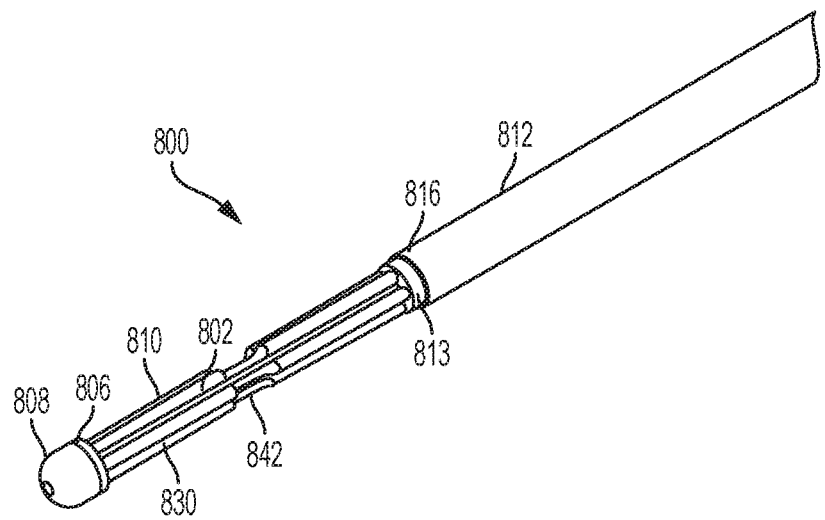

FIGS. 8A to 8C, show the guide device 800 at a transition stage between the collapsed configuration and the deployed configuration from end, side, and isometric views, respectively, according to some examples. As shown, the guide device 800 includes a shaft portion 813 that is attached to (e.g., is continuously formed with) the expandable portion 810. The shaft portion 813 extends from the second end portion 836 of the expandable portion 810 and generally extends through the guide sheath 812 to the proximal end 814 of the guide sheath 812.

As shown in FIGS. 8A to 8C, the guide sheath 812 is removable from around the expandable portion 810 such that the expandable portion 810 is exposed from inside the guide sheath 812. The first arm 830 and aperture 842 are exposed when guide sheath 812 is retracted from around the expandable portion 810. The guide sheath 812 is retractable from around the expandable portion 810, for example by pulling the guide sheath 812 or pushing the expandable portion 810 forward to exit the guide sheath 812. To retract the guide sheath 812, the guide sheath 812 may first be uncoupled from the tip 808, for example, by controlling the proximal end 814 of the guide sheath 812 and the proximal end 804 of the inner shaft 802. An operator controls the guide device 800 from the proximal end 814 of the guide sheath 812 and the proximal end 804 of the inner shaft 802 from outside the patient's body. The operator can advance the expandable portion 810 along the central longitudinal axis in relation to the guide sheath 812, which causes the expandable portion 810 to exit the guide sheath 812 from the distal end 816. As shown in FIGS. 8A to 8C, when the expandable portion 810 is in the collapsed configuration, the first arm 830 is generally linear and in the direction of the central longitudinal axis 818. That is, first arm 830 is straight and parallel to the central longitudinal axis. When the expandable portion 810 is in the collapsed configuration, the outer diameter of the expandable portion 810 is less than the inner diameter of the guide sheath 812.

Figure 9A:
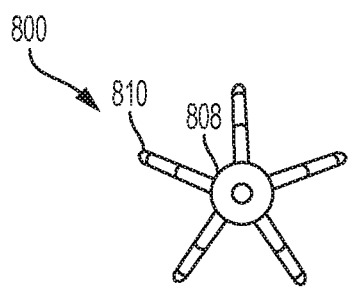
FIGS. 9A to 9C show the guide device of FIGS. 7A to 7C from front, side, and isometric views, where the guide device is shown in a deployed configuration, according to various examples.
Figure 9B:
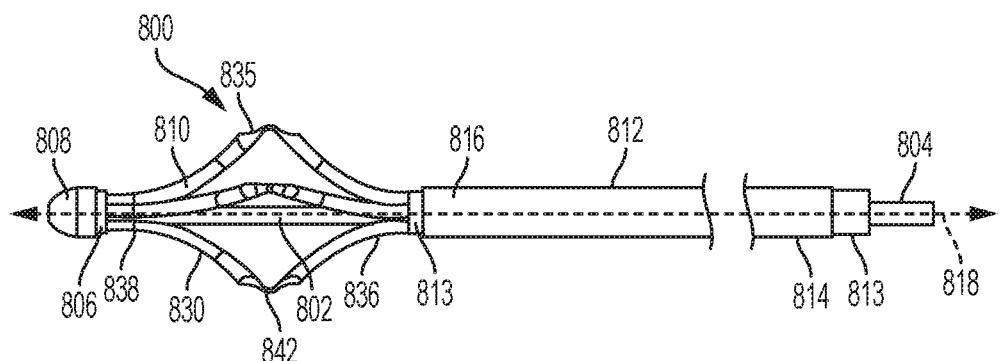
Figure 9C:
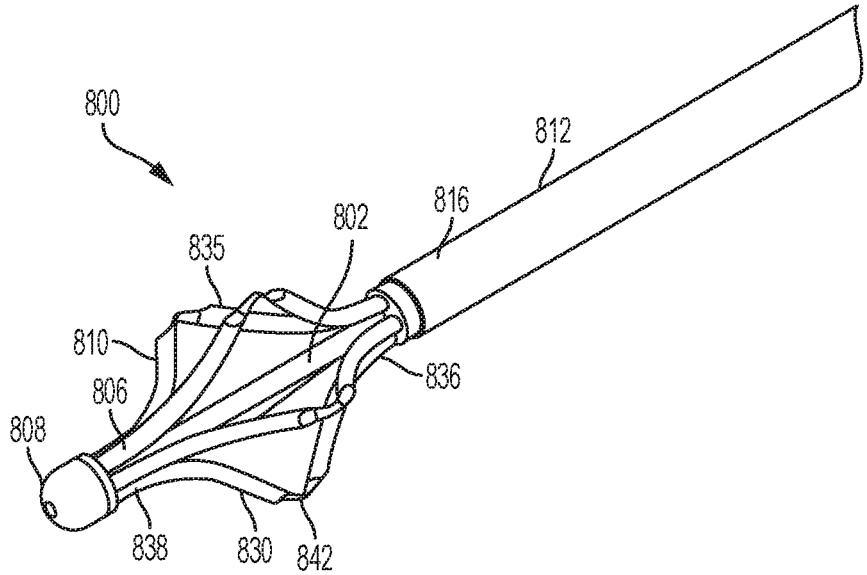

FIGS. 9A to 9C, show the guide device 800 in the deployed configuration with the expandable portion 810 in the deployed configuration from end, side, and isometric views, respectively, according to some examples. As shown in FIGS. 9A to 9C, with the guide sheath 812 removed from around the expandable portion 810, the guide device 800 is controllable into the expanded configuration. That is, in the deployed configuration, the expandable portion 810 is exposed from under the guide sheath 812 and the expandable portion 810 can be expanded outward from the central longitudinal axis 818.

In some embodiments, the expandable portion 810 is transitioned into the expanded position by holding the shaft portion 813 stationary while pulling the inner shaft 802 toward the shaft portion 813. The inner shaft 802 may be slid parallel to the central longitudinal axis to bring the distal end 806 of the inner shaft 802 toward the shaft portion 813. For example, an operator can hold the shaft portion 813 stationary, and pull the proximal end 804 of the inner shaft 802 such that the distal end 806 of the inner shaft 802 moves the tip 808 toward the shaft portion 813. Because the second end portion 838 of the expandable portion 810 is attached to the tip 808 and the first end portion 836 of the expandable portion 810 is attached to the shaft portion 813, moving the tip 808 toward the shaft portion 813 brings the second end portion 838 of the first arm 830 toward the first end portion 836 and compresses the first arm 830 along the central longitudinal axis. Compressing the first arm 830 along the central longitudinal axis 818 between the first end portion 836 and second end portion 838 causes the first arm 830 to bend or collapse and the intermediate portion 835 expands or extends outwardly (for example, in the transverse direction). In this manner, the intermediate portion 835 of the first arm 830 is bent or curved outward from the central longitudinal axis when the expandable portion 810 is in the expanded position.

As shown in FIGS. 9A to 9C, when the expandable portion 810 is in the expanded position, the aperture 842 is extended outwardly such as in the radial direction. That is, the aperture 842 is located at the radially outermost location of the first arm 830 when the first arm 830 is in the expanded position. When the expandable portion 810 is in the expanded configuration, the first arm 830 provides a bias to the aperture 842. In some examples of the expandable portion 810 having more than one first arm 830, the expandable portion 810 expands symmetrically outward from the central longitudinal axis. That is each first arm 830 extends an equal distance outwardly from the central longitudinal axis such that the expandable portion 810 is symmetric about the central longitudinal axis. In addition, the expandable portion 810 may be selectively expanded, such that an outer diameter of the expandable portion 810 is controllable. The expandable portion 810 may be slidably actuated, self-expanding, spring actuated, combinations of the same, or actuated via any other mode of actuation.

Figure 10:
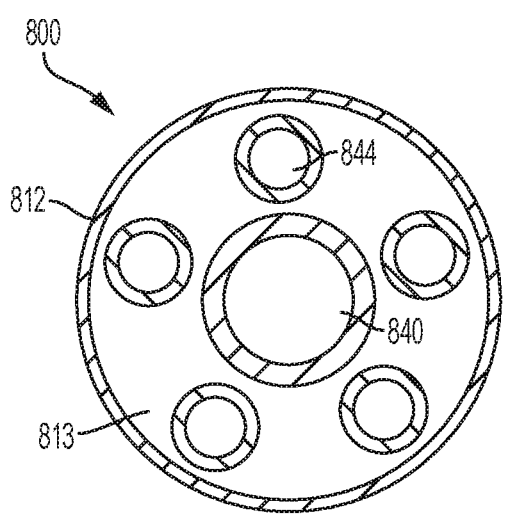
FIG. 10 shows a lumen component of the guide device of FIG. 6, according to various examples.

FIG. 10 shows a transverse cross section of the guide device 800 along line 10-10 shown in FIG. 6. As shown in FIG. 10, the shaft portion 813 is positioned along at least a portion of the length of the guide sheath 812 within the inner diameter of the guide sheath 812. The shaft portion 813 defines an inner lumen 840 that extends along the central longitudinal axis of the shaft portion 813 and a plurality of radial lumens 844 positioned radially around the inner lumen 840. That is, the inner lumen 840 has a length oriented along the central longitudinal axis and the radial lumens 844 are positioned radially around the inner lumen 840 and parallel to the central longitudinal axis. Each of the inner lumen 840 and the radial lumens 844 define a tube or conduit within the shaft portion 813.

The inner lumen 840 is sized to receive the inner shaft 802 shown in FIG. 6 along the central longitudinal axis of the shaft portion 813. The inner lumen 840 has a diameter sized to slidably receive the inner shaft 802. The radial lumens 844 are operatively coupled to the arms 832 of the expandable portion 810 shown in FIG. 6. That is, the end of each one of the radial lumens 844 is integral with the end of one of the arms 832 of the expandable portion 810. Said another way, the radial lumens 844 are connected in series with the arms 832 and each one of the radial lumens 844 is connected to one of the arms 832. The radial lumens 844 are optionally integrally formed with, or are separate, connected components with the arms 832.

Figure 11:
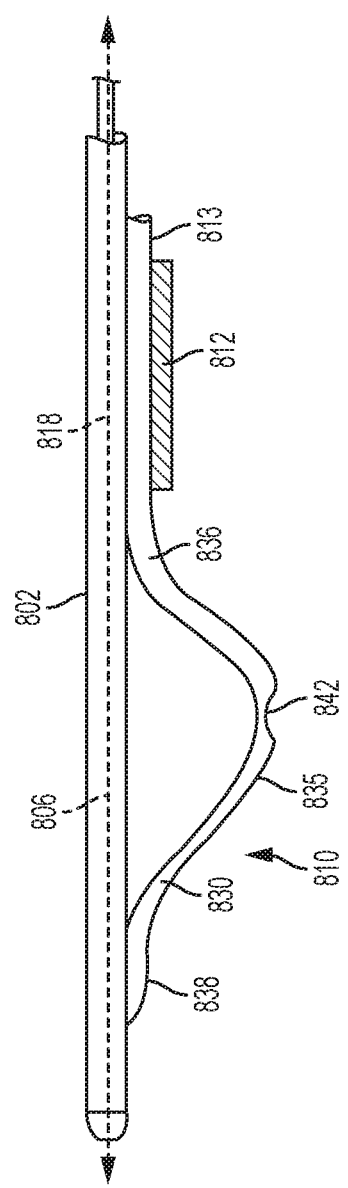
FIG. 11 is a side, partial sectional view of the guide device of FIG. 6 with a single expansion member component, according to various examples.

FIG. 11 is a cut away side view of the guide device 800 showing the expandable portion 810, guide sheath 812, shaft portion 813, first arm 830 and the inner shaft 802 shown in FIG. 6, according to some examples. FIG. 11 shows the inner shaft 802 with the tip removed from the distal end 806. The first end portion 836 of the expandable portion 810 is shown connected to the shaft portion 813. The inner shaft 802 is slidably received within the inner lumen 840 (shown in FIG. 10) of the shaft portion 813, such as along a length of the guide sheath 812. The inner shaft 802 is movable between a first position with the distal end 806 of the inner shaft 802 farther from the distal end 816 of the guide sheath 812, and a second position with the distal end 806 of the inner shaft 802 closer to the distal end 816 of the guide sheath 812. As shown, the first arm 830 is connected to the inner shaft 802 proximate the distal end 806 of the inner shaft 802. As shown, the first end portion 836 and second end portion 838 are drawn together, and the intermediate portion 835 of the first arm 830 is bent or curved with the expandable portion 810 in the expanded position. The aperture 842 is shown along the intermediate portion 835 of the first arm 830.

Figure 12:
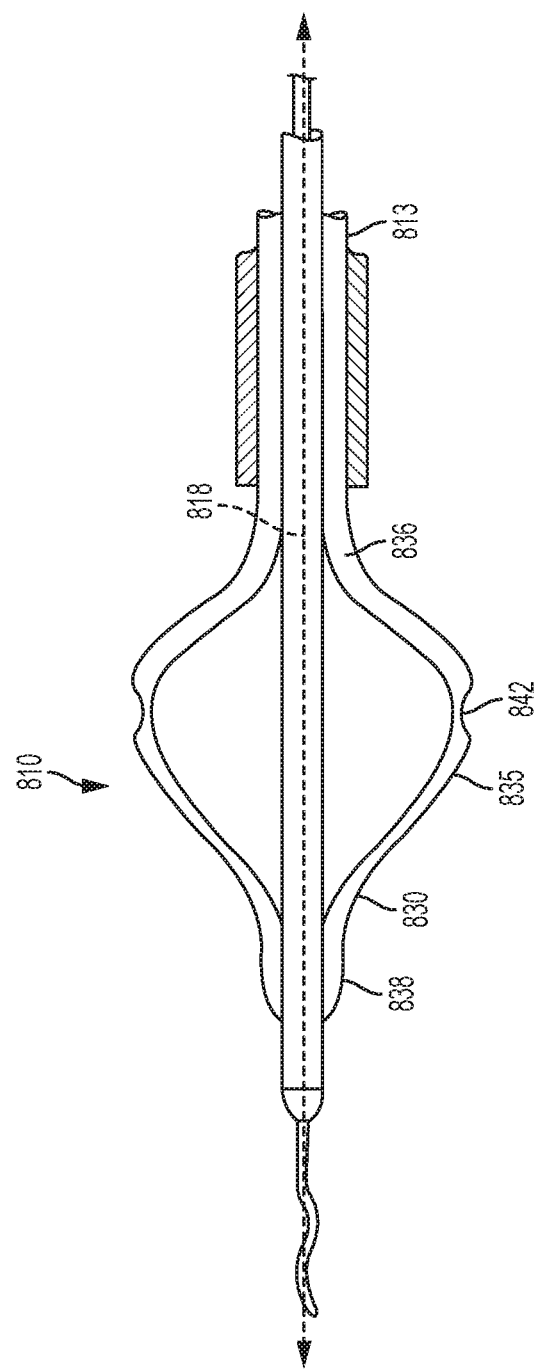
FIG. 12 is a side, partial sectional view of the guide device of FIG. 6 with multiple expansion member components, according to various examples.

FIG. 12 a cut away side view of the guide device 800 showing the expandable portion 810 and shaft portion 813, shown in FIG. 6, according to some examples, and illustrates additional features of the aperture 842. FIG. 12 also shows the first arm 830 of the expandable portion 810 attached to the shaft portion 813. The first arm 830 is connected to one of the radial lumens shown in FIG. 10. As shown in FIG. 12, the first arm 830 defines a curve having a suitable radius when the expandable portion 810 is expanded outward from the central longitudinal axis 818. For example, the first arm 830 defines a curve located along the intermediate portion 835 of the first arm 830 between first end portion 836 and second end portion 838 of the first arm 830. The curve of the first arm 830 is shaped or sized to direct or bias the aperture 842 outward from the central longitudinal axis 818, with an opening that opens in a suitable size and/or direction. The aperture 842 is shaped and located at suitable locations along the curve of the first arm 830.

As previously referenced, the first arm 830 is optionally configured to direct or bias the aperture 842 to face in a suitable direction relative to the central longitudinal axis of the guide device 800. For example, the first arm 830 defines a suitable curve or bias in the expanded configuration and the aperture 842 is located at a suitable location along the curve. As shown, the first arm 830 has the aperture 842 located at an outermost radial portion of the curve such that aperture 842 opens radially outward (e.g., substantially perpendicular to the central longitudinal axis of the expandable portion 810). In other examples, the first arm 830 may have the aperture 842 located along the intermediate portion in a forward facing, or more distal position along the curve, such that the aperture 842 faces at an askew angle from the central longitudinal axis of the expandable portion 810 when in the expanded configuration. The aperture 842 may be positioned to face at an angle of about 10°, about 20°, or about 30°, or about 45°, about 60°, or about 90°, or an angle between any pair of the foregoing values, relative to the central longitudinal axis of the expandable portion 810, for example, although other values are also contemplated.

Figure 12A:
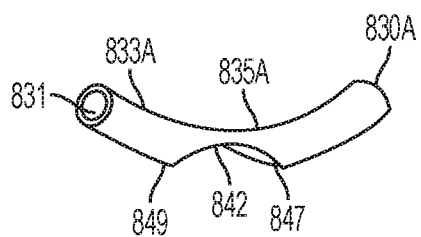
FIGS. 12A to 12F show variations of expansion member components usable with guide device of FIG. 6, according to various examples.

FIGS. 12A to 12F show some design variations for the intermediate portion 835 of the first arm 830 that are employed for one or more of the arms 832 of the guide device 800 as desired. FIG. 12A, shows a first arm 830A according to the example illustrated in FIGS. 11 and 12. That is, FIG. 12A is a partial view of the first arm 830 illustrated in FIGS. 11 and 12 with the first arm 830 cut off at both ends of the intermediate portion 835 for ease of illustration. As shown, the first arm 830A forms a tube shape with an inner diameter defining a lumen 831 along the length of the first arm 830A. The first arm 830A is a substantially unitary body, having a wall 833A extending along the length of the first arm 830A and defining the tube shape. A section of the wall 833A is removed to form the aperture 842. The aperture 842 is in communication with the lumen and forms a guide path from inside the lumen through the aperture to the outside of the first arm 830A. The aperture 842 is generally shaped as a rounded opening having a length corresponding to the central longitudinal axis of the arm and a width corresponding to direction of the circumference of the arm. In alternative configurations, the aperture 842 may be any other suitable shape, such as square, triangular, or a non-symmetrical shape.

As shown in FIG. 12A, when the first arm 830A is viewed from the side, the aperture 842 defines a curve extending in the direction of the central longitudinal axis of the first arm 830A. As also shown, the aperture 842 has a depth that extends between the circumference of the first arm 830A and the longitudinal axis of the first arm 830A when the first arm 830A is viewed from the side. The aperture 842 shown in FIG. 12 has a length that is greater than the diameter of the first arm 830A. The aperture 842 has a curve length which is defined as the length of a path taken from a leading edge 847 to a trailing edge 849 along the curve of the aperture 482. The aperture 842 also has an opening length which is measured in a straight line from the leading edge 847 to the trailing edge 849. The curve length is defined by the shape and dimension of the aperture 842. The radius of the curve defined by the aperture 842 is controllable by bending the first arm 830A farther from a straight position. The opening length is adjustable by changing the radius of curvature of the first arm 830A. Bending the first arm 830A such that the first arm 830A has a curve with a smaller radius causes the aperture 842 to open further along the length and the radius of the curve defined by the aperture 842 increases.

Figure 12B:
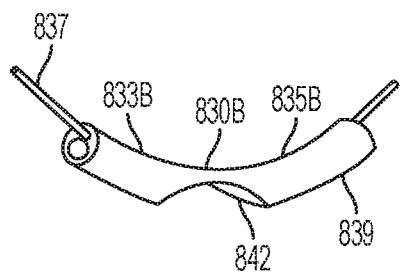

FIG. 12B shows the intermediate portion of another first arm 830B according to various examples. As shown, the first arm 830B comprises a filament 837B or rod having a solid cross-section along the length. The filament 837B optionally extends from the first end portion 836 to the second end portion 838 of the first arm 830 illustrated in FIGS. 11 and 12. That is with the first arm 830B, the filament 837B extends from the shaft portion 813 to the tip 808 of the inner shaft 802. The first arm 830B has a section of a tube 839 coupled to the filament 837B. The tube 839 has an inner diameter defined by a wall 833B extending along the length of the tube 839. The aperture 842 in the first arm 830B is a hole through the wall 833B of the tube 839.

Figure 12C:
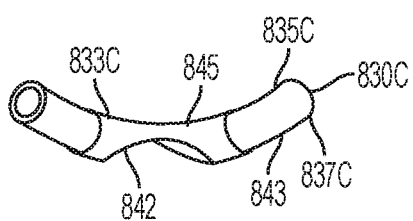

FIG. 12C shows an intermediate portion of another first arm 830C that has a modular design with a first tube 843 along a first portion of the length of the first arm 830C and a second tube 845 along a second end portion of the length of the first arm 830C. The first tube 843 includes a wall 837C that defines a first outer and/or inner diameter and is made of a first material having a first elasticity or flexibility. The second tube 845 has a wall 833C that defines a second outer and/or inner diameter and has a second elasticity or flexibility. The aperture 842 in the first arm 830C is a hole through the wall 833C of the second tube 845.

Figure 12D:
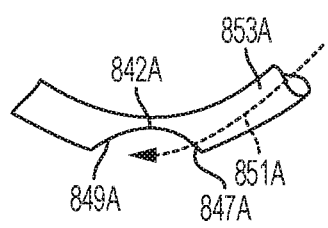
Figure 12E:
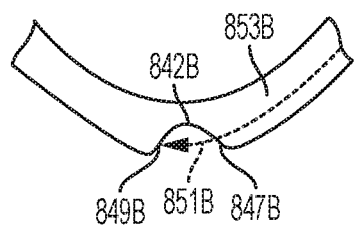
Figure 12F:
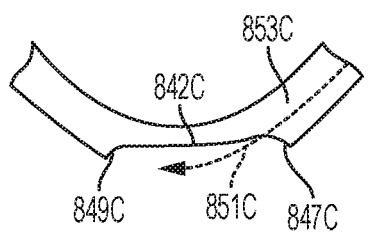

FIGS. 12D to 12F illustrate variations for the aperture 842 employable with any of the foregoing examples of the first arm 830, and more generally the arms 832. The size and/or shape of the aperture 842 helps control the delivery angle that an endoluminal tool is oriented at in relation to the central longitudinal axis of the first arm 830 when deployed. Each of the variations of the aperture 842 also defines an exit location that can be oriented to face in a suitable location. The size and/or shape of the aperture 842 defines the exit location and orients the endoluminal tool at an escape angle outward from the first arm 830. In other words, the first arm 830 and the aperture 842 define a line of travel that the endoluminal tool follows along the length of the first arm 830, through the aperture 842 from the exit location, and at an escape angle outward from the first arm 830.

FIG. 12D shows a first aperture 842A having a first set of dimensions (e.g., length, depth, and radius of curvature) and located at the outermost radial portion of the first arm 830 (e.g. at the apex of curvature of the first arm 830). As shown, the aperture 842A defines a continuously rounded shape when the expandable portion 810 is in the expanded configuration. When the first arm 830 is in the collapsed configuration, a leading edge 847A and trailing edge 849A of the aperture move toward one another and the aperture 842A is reduced in size. As the first arm 830 transitions to the expanded configuration, the first arm 830 bends and the leading edge 847A and trailing edge 849A of the aperture 842A move away from one another. As previously described, the opening length is adjustable and further bending the first arm 830 to increase the radius of the curved defined by the aperture 842A causes the opening length to further increase in size. The aperture 842 defines an exit location 851A, which is the point where the lumen inside the first arm 830 is in communication with the aperture 842A along the leading edge 847A. The exit location 851A can be adjusted to face in a suitable location depending on the shape of the aperture 842A and the degree of curvature of the arm 830. The radius of the curve defined by the aperture 842 and the exit location 851A define a line of travel 853A that an endoluminal tool follows as it passes through the aperture 842A and the escape angle that the endoluminal tool assumes as it extends outward from the first arm 830A.

FIG. 12E shows another aperture 842B. As shown in FIG. 12E, the aperture 842B has another set of dimensions (e.g., length, depth, and radius of curvature). The curve length of the aperture 842B is smaller and the radius of the curve defined by the aperture 842B is smaller than that of the aperture 842A in FIG. 12D. The aperture 842B is shaped with the leading edge 847B and trailing edge 849B closer together, and the largest available opening length is smaller than the aperture 842A in FIG. 12D. The line of travel 853B is controlled between the leading edge 847A and trailing edge 849B. The escape angle that an endoluminal tool assumes as it extends outward from the first arm 830 can be controlled by the orientation of the exit location 851B. The line of travel 853B and the escape angle in FIG. 12E is more restrained than the line of travel 853A formed by the aperture 842A in FIG. 12D. The exit location 851B defined by the aperture 842B of FIG. 12D, faces closer toward the central longitudinal axis than the exit location of the aperture 842A in FIG. 12D at the same degree of curvature of the first arm 830. That is, in order to orient the exit location 851B of the aperture 842B in FIG. 12E at an angle approaching 90° from the central longitudinal axis, the first arm 830 has a smaller radius of curvature than if the first arm 830 included the aperture 842A defining the exit location 851A in FIG. 12D.

FIG. 12F shows another aperture 842C. As shown in FIG. 12F, the aperture 842C is shaped with a larger opening than the aperture 842A shown in FIG. 12D. The aperture 842C in FIG. 12F is shaped with a substantially open configuration such that the leading edge 847C and trailing edge 849C are farther apart. The aperture 842C has a greater curve length than the aperture 842A shown in FIG. 12D and the leading edge 847C and trailing edge 849C are farther apart along the first arm 830. This allows the first arm 830 to be bent further than the aperture 842A shown in FIG. 12D and allows the aperture 842C to form a greater opening length. The line of travel 853C is further from the trailing edge 849C than the line of travel 853A formed by the aperture 842A in FIG. 12D. In this manner, the exit location 851C defined by the leading edge 847C can be positioned to face radially outward more than the exit location 851A in FIG. 12D. The escape angle of an endoluminal tool deployed from the aperture 842C is a higher angle from the central longitudinal axis than the escape angle of an endoluminal tool deployed from the aperture 842A in FIG. 12D. That is the exit location 851C in FIG. 12F is oriented closer to 90° to the central longitudinal axis than the exit location 851A in FIG. 12D. By selecting the length, width and radius of curvature of the aperture 842, the escape angle of an endoluminal tool outward from the first arm 830 can be controlled to a suitable angle to the central longitudinal axis of the first arm 830.

Figure 13:
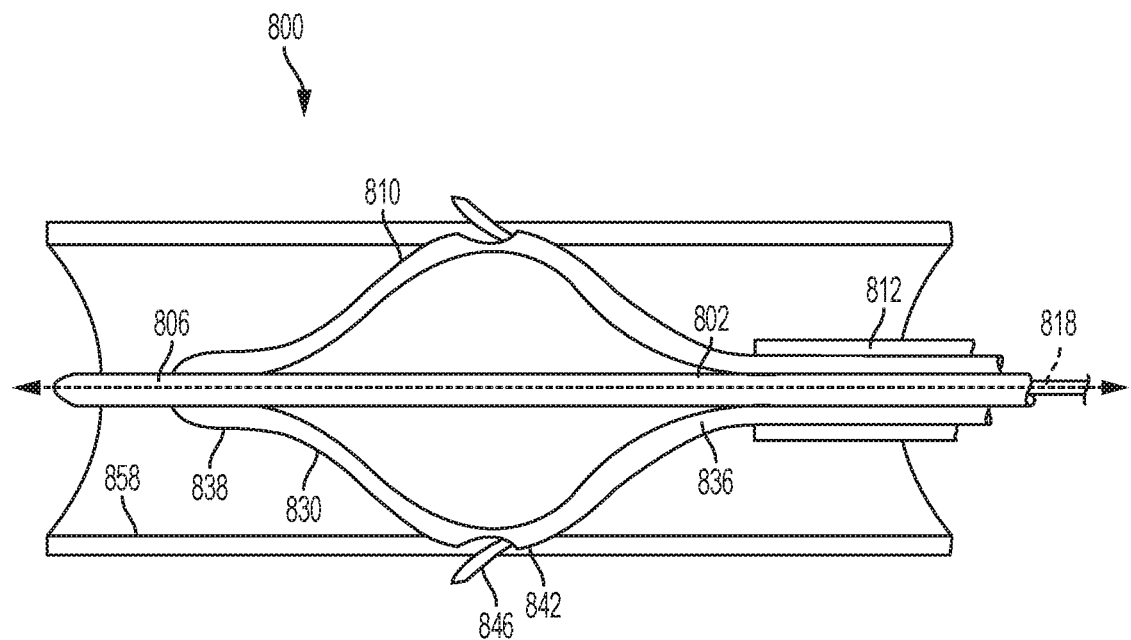
FIG. 13 shows delivery of a tool from a guide device, according to various examples.
Figure 13A:
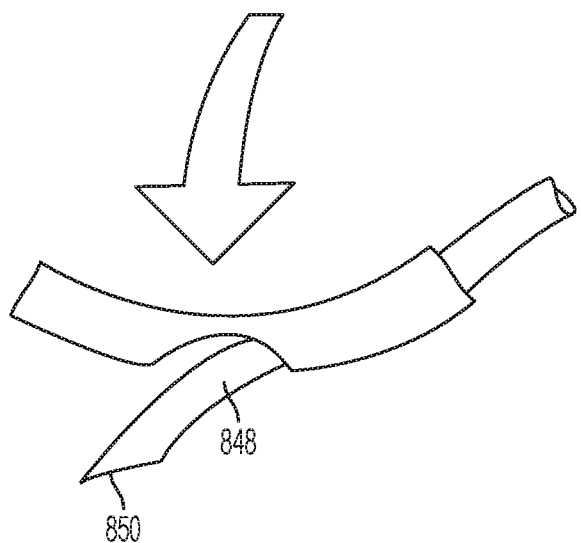
FIG. 13A is an enlarged view taken from FIG. 13, according to various examples.

FIG. 13 is a partial cut away, side view of the guide device 800, according to some examples. As shown, the guide device 800, and in particular the expandable portion 810 is in the expanded configuration with an endoluminal tool 846 deployed from the aperture 842. The inner shaft 802 is movable in relation to the guide sheath 812, and may be used to move the distal end 806 closer to and further away from the guide sheath 812, for example by moving the inner shaft 802 in relation to the guide sheath 812. The second end portion 838 of the first arm 830 is connected to the distal end 806 of the inner shaft 802, and the inner shaft 802 can move the second end portion 838 of the first arm 830 relative to the first end portion 836 of the first arm 830 along the central longitudinal axis 818.

As shown in FIG. 13, the guide device 800 is configured to deploy an endoluminal tool 846. In some examples, the endoluminal tool 846 is located within the first arm 830 when the expandable portion 810 is in the collapsed configuration. When the expandable portion 810 is in the expanded configuration, the endoluminal tool 846 can be deployed from the first arm 830 through the aperture 842. The expandable portion 810 may deploy more than one endoluminal tool 846 through a single arm or multiple arms 832. For example, each of the arms 832 may house an endoluminal tool, such as the endoluminal tool 846. The arms 832 may then be utilized to deploy an endoluminal tool 846 that is different than an endoluminal tool 846 in another one of the arms 832. That is, each of the arms 832 may define a separate lumen, each separate lumen may be configured to receive an endoluminal tool 846, and each separate lumen may be configured to deploy and deflect a separate endoluminal tool 846. The first arm 830 and/or aperture 842 are shaped to direct or bias the endoluminal tool 846 in a suitable direction away from the central longitudinal axis 818, when deployed. The endoluminal tool 846 may be biased to extend from the central longitudinal axis of the guide device 800 at an escape angle of about 10°, about 20°, about 30°, about 40°, about 50°, about 60°, about 70°, about 80°, or about 90°, or an angle between any pair of the foregoing values from the central longitudinal axis of the guide device 800, for example, although other values are also contemplated. The first arm 830 and/or aperture 842 can be deployed from a remote location and position the endoluminal tool 846 in-situ in relation to the central longitudinal axis of the guide device 800.

The endoluminal tool 846 is any tool that is suitable for deployment and/or use within a lumen 858, which may be a lumen of a vessel within a body of a patient and/or an implanted medical device. The endoluminal tool 846 may be an angioscope, an elongate member, a needle, an infusion needle, a biopsy needle, an ablation device, a stent, a stent graft, a drug delivery tool, a biopsy punch, an endotack, a suture device, a fixation device, a radiopaque marker, an occlusion coil, an occlusive agent, a sensor, or any of a variety of tools. The endoluminal tool 846 may be an endovascular tool (i.e. a tool for use in endovascular procedures), for example, a puncturing tool, a piercing catheter, a re-entry device, a dual-lumen re-entry device, or other endovascular tools. In a further example, the endoluminal tool 846 may be a needle or needles, such as microneedles. The endoluminal tool 846 may include a device for piercing, drilling, or cutting a lumen wall from the inside. The endoluminal tool 846 may include an end effector 848 that may include a pointed tip 850. The endoluminal tool 846 may include a needle that may be deflected from the first arm 830 to firm a first path, such as through a vessel wall, and the endoluminal tool 846 may include a guide wire that may be inserted along the first path. The endoluminal tool 846 may include a needle configured to be repeatedly inserted through a vessel wall to form multiple paths, and may include a guide wire that is configured to be inserted through each of the multiple paths formed by the needle. The endoluminal tool 846 may be deployed to simultaneously deliver multiple attachment devices, such as endotacks, for example to attach a medical device to a vessel wall from within the vessel. The endoluminal tool 846 may be deployed from the first arm 830 to create a hydro-dissection within the lamina of a vessel wall. In some instances, the endoluminal tool 846 may be deployed to deliver a multi-component substance, such as an epoxy resin comprising multiple epoxies, to the hydro-dissection within the lamina of the vessel wall.

The endoluminal tool 846 may have a pre-shaped curve, and/or may have a shape memory. As an example, the endoluminal tool 846 having a preshaped curve can be deployed from the first arm 830 and contact a vessel wall, such as a wall of a vein, artery, or stent at an angle from the central longitudinal axis of the guide device 800. The endoluminal tool 846 can be controlled to contact the vessel wall from within the lumen at a suitable angle and in some examples, penetrates the vessel wall. In examples of an endoluminal tool 846 having a preshaped curve, the pre-shaped curve and/or shape memory directs the endoluminal tool 846 after being deployed from the expandable portion 810. The endoluminal tool 46 may be a transvascular tool (i.e. a tool that is capable of accessing across the wall of a blood vessel or similar vessel, such as controllably accessing a location outside a vessel from a starting location that is within the vessel). In some examples, the endoluminal tool 846 may include both a transvascular tool and a needle so that a therapeutic agent may be delivered outside of the vessel once the lumen wall has been pierced by the transvascular tool.

As shown, the first arm 830 houses the endoluminal tool 846 and directs the endoluminal tool 846 using the curve or bias of the first arm 830. The aperture 842 is dimensioned and configured to direct the endoluminal tool 846 at a suitable angle relative to the first arm 930. In various examples, the endoluminal tool 846 is positioned to face at an angle of about 10°, 20°, or 30°, or about 45°, 60°, or 90°, or any angle between the foregoing values from the central longitudinal axis 818 of the expandable portion 810, although other values are also contemplated. In some examples, more than one of the arms 832 contains an endoluminal tool, such as the endoluminal tool 846. In examples having more than one endoluminal tool 846, each endoluminal tool 846 may be the same, or one or more arms 832 may include an endoluminal tool 846 that is different than an endoluminal tool 846 in another one of the arms 832.

Figure 14A:
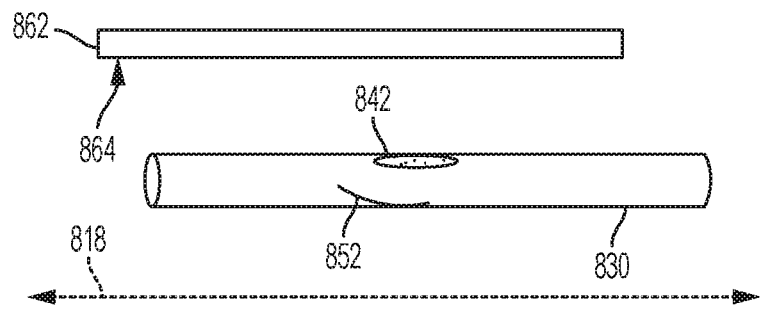
FIGS. 14A to 14D are schematic views illustrating a method of deploying a guide device to orient and operate a tool in association with a medical procedure, accordance with various examples.
Figure 14B:
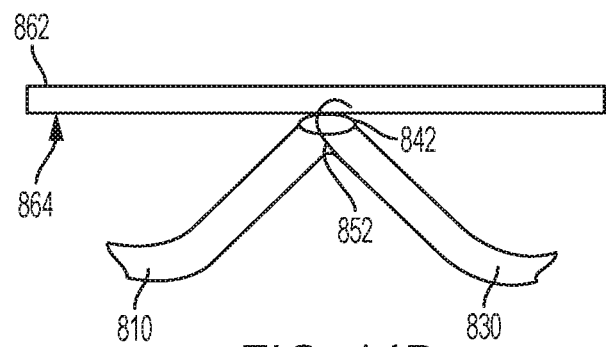

FIGS. 14A to 14D are schematic representations of the first arm 830 and corresponding endoluminal tool 846 at various stages of deployment, according to some methods of use. FIGS. 14A to 14D also illustrate a deployment guide 852 that can be included with various embodiments of the first arm 830. As shown in FIG. 14A, the deployment guide 852 is located within the arm 830 when the arm is in the collapsed configuration. The deployment guide 852 is located along the inside of the arm 830 and positioned to correspond with the aperture 842. The deployment guide 852 is shaped and oriented to direct an endoluminal tool 846 out of the arm 830 and through the aperture 842. The deployment guide 852 may define a curve, as shown in FIG. 14B, and direct the endoluminal tool 846 along the curve when the endoluminal tool 846 is deployed. The deployment guide 852 can be controlled as the deployment guide 852 passes through the aperture 842 and away from the arm 830 by the user, such as through a wall of a vessel 862. The deployment guide 852 can be formed with a material having a shape memory.

With the guide device 800 appropriately positioned at the treatment site, some deployment processes include deploying the endoluminal tool 846 to the treatment site through the first arm 830 by longitudinally sliding the tool 846 within the first arm 830. As shown in FIG. 14A, the first arm 830 is first exposed and oriented as desired (e.g., with the aperture 842 facing toward a surface 864 of the lumen of a vessel 862 to be accessed). As shown in FIG. 14B, the first arm 830 of the expandable portion 810 is transitioned to the expanded configuration such that the first arm 830 is substantially curved and deflected toward the vessel wall with the aperture 842 biased against the lumen of the vessel 862. As shown, the first arm 830 is in contact with the surface 864 of the vessel 862 and the aperture 842 directs the endoluminal tool 846 against the surface 864. The endoluminal tool 846 is deployed from the first arm 830 and is guided toward the surface 864 by the deployment guide 852. As shown, the deployment guide 852 penetrates the surface 864 of the vessel 862. The endoluminal tool 846 extends through the aperture 842 toward the surface 864 and is directed into the surface 864 of the lumen of a vessel 862 along a guide path defined by the deployment guide 852. The deployment guide 852 can be used to guide the endoluminal tool 846 through the surface 864 of the vessel 862 to a treatment site along the guide path.

Figure 14C:
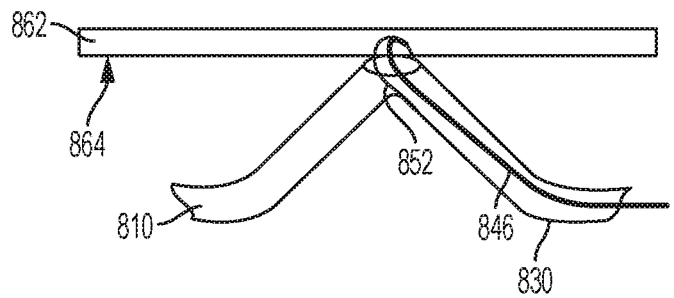

FIG. 14C shows the expandable portion 810 maintained in the expanded configuration with endoluminal tool 846 deployed. The endoluminal tool 846 follows the curve of the deployment guide 852 through the surface 864 of the vessel 862, and optionally penetrates out from the wall of the vessel 862 through the surface 864. The endoluminal tool 846 may be used to deliver a therapy such as therapeutic agent or therapeutic method to the vessel 862. As shown in FIG. 14C, the endoluminal tool 846 is a needle that may be used to place a suture into the wall of the vessel 862. The endoluminal tool 846 is guided into and back out of the surface 864 of the vessel 862 and places the suture into the vessel wall. In another configuration, the endoluminal tool 846 is a pre-curved or self-curving tool and deploys out of the aperture 842 without a deployment guide.

Figure 14D:
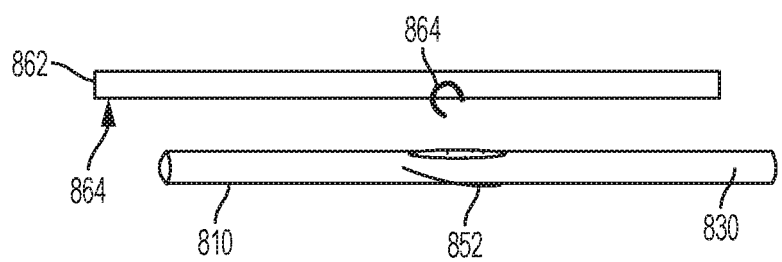

FIG. 14D shows the expandable portion 810 after the endoluminal tool 846 has been retracted back into the first arm 830 and the expandable portion 810 is transitioned back into the collapsed position. The endoluminal tool 846 may be sized and shaped such that advancing and retracting the endoluminal tool 846 into and from the vessel 862 is carried out with minimal trauma to the vessel 862. The endoluminal tool 846 is retracted into the expandable portion 810 by slidably receiving the endoluminal tool 846 into the first arm 830. The expandable portion 810 is collapsed by reducing the outer diameter of a space defined by the first arm 830 such that the expandable portion 810 can be withdrawn into the guide sheath 812. With the expandable portion 810 retracted into the guide sheath 812, the guide device 800 is removed from the vessel 862. As shown, the guide device 800 provides an endoluminal access device which allows a user to access a target side inside a lumen from a remote location with minimal trauma to the lumen proximate the target site.

Figure 15:
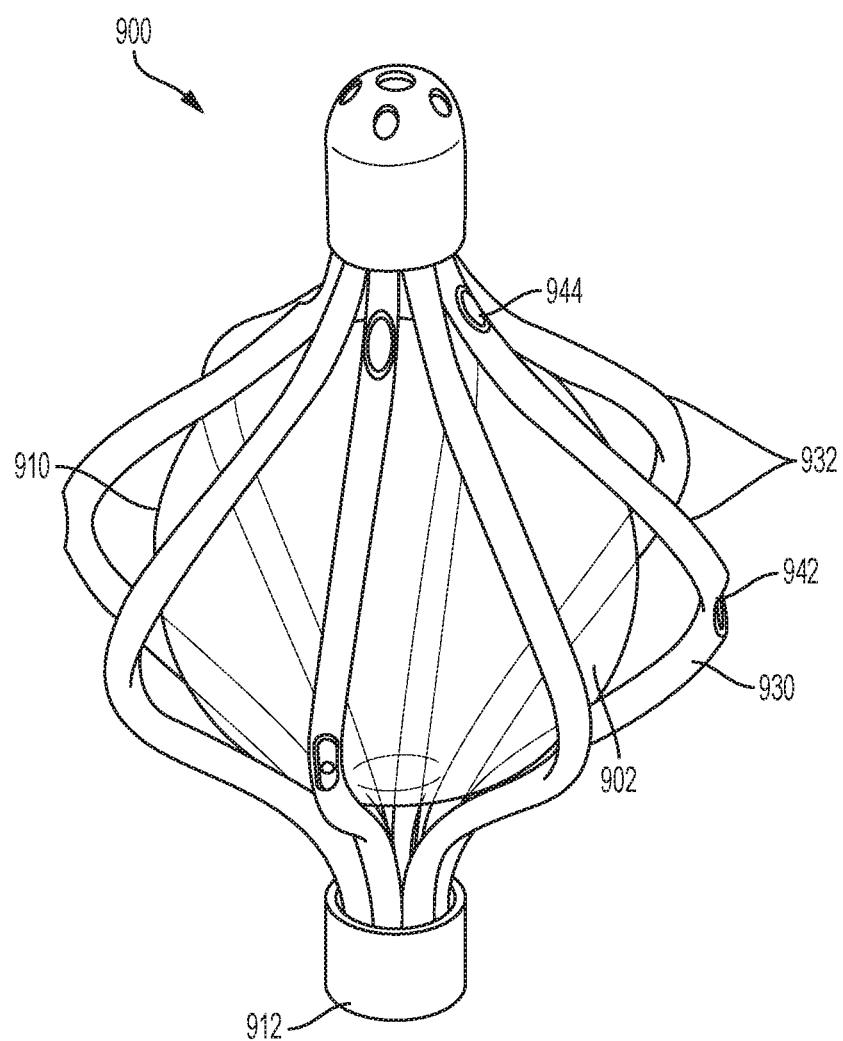
FIG. 15 shows another guide device, according to various examples.

FIG. 15 includes another guide device 900. As shown, the guide device 900 includes an expandable portion 910 and a guide sheath 912. The expandable portion 910 includes at least a first arm 930. In some embodiments, the expandable portion 810 includes two or more arms 932. The various arms 932 are optionally substantially similar, and thus description of the features of the first arm 930 will be understood to be applicable to the remaining arms 932 as well. The first arm 930 includes an aperture 942. As shown, the first arm 930 includes a second aperture 944.

As shown in FIG. 15, an inflatable member 902 is located within a space defined between the arms 932. The inflatable member 902 is a device capable of expanding in response to an increase in pressure within the inflatable member 902. For example, the inflatable member is a balloon, bladder, or inner tube. The inflatable member 902 has a first outer diameter in the collapsed configuration such that the inflatable member 902 fits within a space defined between the arms 932 while the arms 932 are in a collapsed position and sized to fit within the guide sheath 912. The inflatable member 902 is configured to be expanded using pressurized actuation, such as using pneumatic or hydraulic pressure to inflate the inflatable member 902. In some embodiments, inflating the inflatable member 902 may be carried out by an inflation tube (not shown) that extends the length of the guide sheath 912 and provides pressurized fluid, such as gas or liquid, into the inflatable member 902. In some instances, the inflatable member 902 allows fluid flow through a vessel to pass the inflatable member 902 while the inflatable member 902 is positioned within the vessel. For example, the inflatable member 902 can be configured to allow perfusion through a vessel throughout all stages of expansion, such as when the inflatable member 902 is fully deflated, when the inflatable member is fully expanded, and the various levels of expansion in between. In another example, the inflatable member 902 is configured to cut off fluid flow through a vessel. For example, the inflatable member 902 can be configured to cut off perfusion through a vessel when the inflatable member 902 is at a suitable degree of expansion, and/or throughout various stages of expansion.

Upon inflation, the inflatable member 902 pushes the arms 832 outward, and outwardly expands the expandable portion 910. The inflatable member 902 provides structural support to the expandable portion 910 while the expandable portion 910 is in the expanded position. The outer diameter of the expandable portion 910 is selectable by controlling the outer diameter of the inflatable member 902. The expandable portion 910 can be transitioned to the collapsed configuration by deflating the inflatable member 902. The inflatable member 902 is deflated by reducing the pressure within the inflatable member 902. The inflatable member 902 may be deflated and then confined by the expandable portion 910 when the expandable portion 910 transitions back to its collapsed configuration. The inflatable member 902 may be of sufficient size after transitioning into the collapsed configuration to catheter the expandable portion 910 into the guide sheath 912 with the inflatable member 902 positioned within a space between the arms 932.

As shown in FIG. 15, the guide device 900 allows continuous fluid flow through a vessel that the guide device 900 is located in, throughout deployment of the guide device 900. That is, the guide device 900 does not occlude the vessel, but allows at least some fluid flow through the vessel (e.g., around the guide sheath 912 and past/through the expandable portion 910). The guide device 900 allows fluid flow through spaces defined between individual arms 832 and between the arms 832 and the inflatable member 902 when the guide device 900 is in the expanded configuration. For example, when positioned within a blood vessel, the guide device 900 is sized and configured such that an open interior is defined between individual arms 832 and between the arm 832 and the inflatable member 902 such that blood can flow around the inflatable member 902. In this manner, at least some fluid flow, such as aortic downstream perfusion, is allowed past the guide device 900 when the guide device 900 is being inserted through a vessel, when the guide device 900 is in the collapsed configuration, and/or when the guide device 900 is transitioning between the collapsed configuration and the expanded configuration.

FIGS. 16A-16F and 17a-17B show various exemplary uses for the guide device, according to some embodiments. As discussed above, in some instances, the guide device 1000 can be used to pierce a vessel 1020 and to deliver a therapeutic agent 1040, such as an occlusive material or self-hardening or self-expanding gel, to the outside of the vessel. The therapeutic agent is capable of altering the anatomy of the vessel 1020 by applying a force to the outside surface of the vessel 1020 as the agent hardens and/or expands. In some instances, this may force the lumen wall 1020 inward, reducing the diameter of the vessel 1020 any amount as desired or occluding the vessel 1020 completely.

FIGS. 16A-16F show a guide device 1000 configured to deliver a therapeutic agent to the outside of the vessel 1020, according to some embodiments. As discussed above, the guide device 1000 is delivered to the desired treatment site within the vessel and expanded, as shown in FIG. 16A. Once expanded, one or more endovascular tools 1080 may be moved through one or more arms 1060 of the device to penetrate the vessel 1020 (FIG. 16B). The endoluminal tool 1080 then delivers the therapeutic agent 1040 to one or more locations outside of the lumen wall 1020 (FIG. 16C). As the therapeutic agent 1040 hardens, it applies an occlusive force or pressure to the outside of the lumen wall 1020, effectively constricting the vessel 1020 by at least partially restricting or collapsing the lumen wall 1020 to a smaller diameter (FIG. 16D) or, in some examples, occluding the vessel 1020 completely. Suitable amounts of the therapeutic agent 1040 may be delivered to collapse the diameter of the vessel any amount as desired. In some examples, a reduction in fluid flow through the vessel 1020 may be desired but a total and complete occlusion may not be, such as when adjusting fluid pressure within the vessel 1020 and/or adjusting pressure or fluid flow to various areas of the body.

In one example, the device 1000 can be used to treat heart failure in a patient and/or other cardiovascular diseases such as hypertension and hypotension. In certain instances, heart function of a patient may be compromised by buildup of excess fluid (e.g., hypervolemia) in the body. The buildup of fluid may increase fluid accumulation, principally in the tissues, and increase pressure in the various circulations. The increased pressure in and of itself or in combination with an already failing heart may further harm the patient. In certain instances, patients with heart failure (such as late-stage heart failure) have decreased cardiac output (e.g., amount of blood pumped by the heart per minute), which can lead to decreased diuresis.

For example, the guide device 1000 can reduce the diameter of the vessel 1020 to improve perfusion of one or more organs, such as the heart or the kidneys, or alter hemodynamics or other fluid dynamics within a vessel. As opposed to using an implanted endovascular device, delivering the therapeutic agent 1040 a location outside of the vessel 1020, as described above, can constrict the vessel 1020 and create a flow diversion, thus improving perfusion, without requiring implantation of a device inside of the vessel 1020. The amount of therapeutic agent 1040 can be altered to induce the desired restriction of the vessel 1020. Flow dynamics within the vessel 1020 can be manipulated by narrowing the diameter of the vessel 1020 or otherwise altering the anatomy of the vessel 1020. This may either decrease or increase fluid velocity through certain areas of the body.

The device 1000 can facilitate diverting excess fluid from tissues by manipulating renal blood flow hemodynamics to induce a physiologically mediated therapeutic response. The device 1000, in certain instances, facilitates increases natural diuresis and lessens buildup of excess fluid and diverts excess fluid from around the heart (and/or chest cavity) by restricting the vessel 1020 (which may be the aorta distal to the renal arteries). More specifically, the device 1000 can facilitate increase of blood pressure at an ostium of a renal artery of a patient by manipulating the anatomy of the aorta distal to the renal arteries (by insertion of the therapeutic agent around the abluminal surface of the aorta, for example) to increase pressure across the kidney relative to the venous outflow pressure. This may cause more blood to flow through the kidney, which allows the kidney to increase fluid filtration resulting in improved diuresis and less fluid retention.

Thus, the device 1000 may facilitate a non-pharmaceutical-based option for regulating fluid retention. The device 1000 enables a patient's own kidneys to regulate fluid uptake and removal without pharmaceutical intervention. The device 1000, in certain instances, enable continuous and controlled fluid removal.

In another example, the device 1000 may facilitate increase blood flow into at least one of the renal arteries and divert fluid away from the heart by manipulating the anatomy of the aorta distal to the renal arteries (by insertion of the therapeutic agent around the abluminal surface of the aorta, for example). In a patient suffering from heart failure, fluid overload may be caused (at least in part) by insufficient blood flow through the kidneys resulting from compromised cardiac output.

In certain instances, the device 1000 may facilitate increase blood flow into at least one of the renal arteries while maintaining a substantially unrestricted blood flow within the aorta proximal to the renal arteries, which may focus blood flow into the one or both of the renal arteries. For example, the device 1000 may insert a therapeutic agent to restrict the aorta proximal to the renal arteries by reducing the diameter of the aorta proximal to the renal arteries. This restriction may direct blood flow to other areas supplied by the aorta such as the celiac artery, the superior mesenteric artery, or the brain. Thus, in certain instances, the device 1000 may be arranged within the aorta of the patient at least partially distal of the renal arteries. The result may be increased blood flow to at least one of the kidneys by way of the increased blood flow to one or both of the renal arteries, which may increase fluid removal and decrease pressure on the patient's heart.

As discussed above, in some instances, the device 1000 may facilitate a non-pharmaceutical approach to increasing urine production and/or modifying systemic blood pressure. Patients may experience drug resistance, inaccurate dosing, or undesirable side effects. When drugs fail, aquapheresis or hemodialysis may be used to filter fluid directly from blood, however, these solutions are relatively invasive and disruptive to patient lifestyle. In addition, aquapheresis or hemodialysis may also produce hemodynamic instability with related cardiovascular complications, kidney damage, infection, and/or require capital equipment.

In certain instances, the device 1000 may facilitate a long-term or chronic physiological change in the patient. By altering flow into the kidneys, a neuro-hormonal response may be induced that effects a change in the patient to move toward normal kidney functioning. The kidneys are a feedback regulator of systemic pressure through the patient's body. Thus, the device 1000 facilitates a non-pharmaceutical means of influencing the kidneys' natural feedback mechanisms to regulate systemic pressure. Adjusting the aortic flow resistance may influence renal artery pressure and/or flow rate, which, in turn, can manifest as transient or long-lasting alterations in systemic blood pressure. The changes induced by the device 1000, in renal-mediated blood pressure levels, may have therapeutic benefits in and of themselves. Likewise, changes induced by the device 1000 in renal-mediated blood pressure levels may be used in combination with various blood pressure medications to optimize blood pressure management on an individualized basis. In certain instances, the device 1000 may facilitate increase a resistance to blood flow, within the aorta distal to the renal arteries by approximately 10% to 30% as compared to normal flow. The device 1000 may occlude the aorta distal to the renal arteries by approximately 10% to 30 to increase blood flow blood flow into the kidneys. In certain instances, occluding the aorta distal to the renal arteries (increasing resistance to blood flow therethrough) at a percentage greater than approximately 70%, may decrease blood flow to the kidneys based on the kidneys' natural feedback mechanisms to regulate systemic pressure.

In other examples, the device 1000 can be configured to induce stenosis of the aorta (e.g., vessel 1020) of the patient at least partially distal of the renal arteries, for example, between 40% and 80% and alter blood flow into at least one branch vessel of the aorta (e.g., one or both of the renal arteries) while maintaining a substantially unrestricted blood flow within the aorta proximal to the at least one branch vessel (e.g., one or both of the renal arteries). The aorta (e.g., vessel 1020) may be restricted by delivering the therapeutic agent 1040 to a location outside of the vessel 1020, as described above. In certain instances, the induced stenosis is between 50% and 70%. Clinically, measurement of ankle pressure, Doppler ultrasound velocity, ankle-brachial index, or other hemodynamic parameters in the lower limbs can be employed to optimize the magnitude of the induced stenosis while ensuring adequate limb perfusion. The magnitude of the induced stenosis may be adjusted based on the amount of therapeutic agent 1040 delivered. In addition, the device 1000 may be implanted into another vessel 1020 of the patient that leads into an organ. In these instances, the device 1000 may induce stenosis of the vessel 1020 into which the device 1000 distal of location at which the device 1000 is implanted between 40% and 80%. In addition, implanting the device 1000 in this manner alters blood flow into the organ that the vessel 1020 leads into while maintaining a substantially unrestricted blood flow within the vessel 1020 proximal to the location of implantation.

In some examples, complete occlusion of the vessel 1020 may be beneficial, such as when diverting flow to and/or from a certain area of the body. Examples of such instances include starving a tumor of blood supply, reducing the appearance of varicose veins, and/or other similar therapies.

One specific example includes reducing the diameter of the ovarian vein after pregnancy, which can dilate due to valve failure or obstruction of flow during pregnancy. Reducing blood flow through the ovarian vein effectively reduces the appearance of varicose veins around the ovary and, in some cases, the pelvis.

In another example, a suitable amount of the therapeutic agent 1040 in the form of a self-hardening material may be injected around the outer surface of an aneurysm within the vessel 1020, such as a brain aneurysm, aneurysm of the aorta or aneurysm near the renal arteries. As the material hardens, it encases the aneurysm and prevents further expansion of the aneurysm. This eliminates the need for other, more invasive treatments including implantation of stents, grafts, stent-grafts, and/or other endoluminal medical devices or surgical replacement of the diseased segment altogether, which may cause undesirable side-effects or be difficult to perform in smaller or harder to reach areas of the body.

A method for treating various vascular conditions such as aneurysms includes delivering the guide device to the desired treatment area, deploying the guide device as discussed above, simultaneously fenestrating (e.g., penetrating) the lumen wall of the aneurysm in at least two locations, and injecting the therapeutic agent around the outer surface of the aneurysm such that the agent substantially surrounds and encases the aneurysm. The guide device can then be collapsed and removed from the vessel 1020. FIG. 16E shows a suitable amount of therapeutic agent 1040 delivered to completely occlude the vessel 1020. Once the vessel 1020 has been occluded or the diameter of the vessel 1020 has been reduced as desired, the guide device 1000 is collapsed and removed from the vessel (FIG. 16F).

Figure 17A:
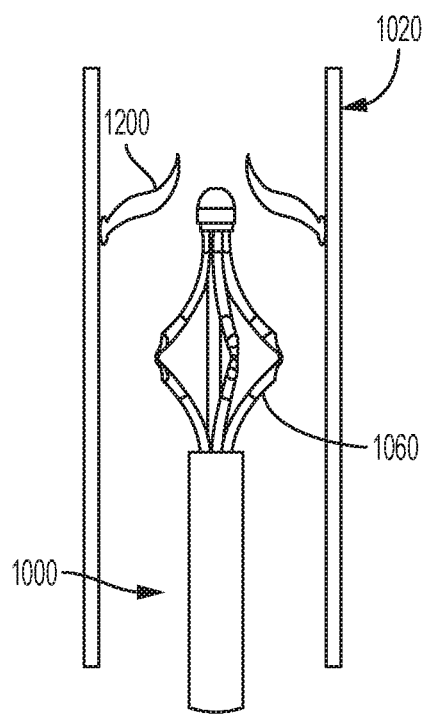
FIGS. 17A to 17B are schematic views illustrating a method of delivering an occlusive agent to an area outside of a vessel, according to various examples.
Figure 17B:
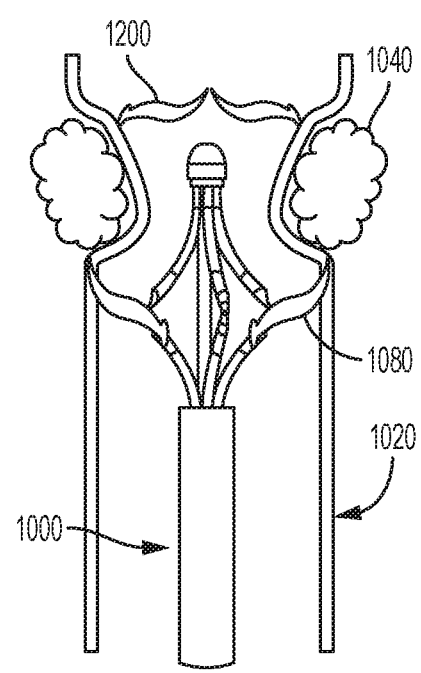

FIGS. 17A-17B show a guide device 1000 configured to deliver a therapeutic agent 1040 to a location proximate a valve 1200, according to some embodiments. 17A shows a vessel with a valve 1200. The valve 1200 includes a pair of valve leaflets that are defective. In certain instances, the valve leaflets may be biased in a relaxed or open position, which may put increased pressure on vessel walls and/or cause blood to pool in various parts of the body.

FIG. 17B shows the therapeutic agent 1040 (e.g., an occlusive material and/or self-hardening gel) delivered to a location outside the vessel 1020 (or heart) and proximate the valve 1200. As shown in FIG. 17B, the therapeutic agent 1040 can be delivered in a similar manner as described above for FIGS. 16A-16E. In certain instances, the therapeutic agent 1040 may decrease the diameter of the vessel 1020 proximate the valve 1200, thereby buttressing the valve 1200 and biasing the valve 1200 in a closed position. This may allow for improved valve leaflet coaptation and, subsequently, relieve venous insufficiency, for example. Although various applications for delivery tools have been referenced by way of example, additional examples of treatments that may be provided include treatment of aneurysms, dissections, and other pathologies located in the aortic arch, treatment of coronary artery disease, peripheral vascular diseases, portal hypertension, carotid artery disease, renal vascular hypertension, and other conditions affecting anatomical conduits, delivery of drugs or other implantable devices to specific treatment sites, location and direction of endovascular tools to branch vessels from within a main vessel, such as to a branch-main vessel junction.

Moreover, the systems and methods of the various examples of the guide device shown in FIGS. 1 to 17 are provided as an example of the various features of the expandable portion, first arm, aperture, and endoluminal tool described. Although the combination of the various illustrated features is clearly within the scope of the disclosure, these examples and the corresponding illustrations are not meant to suggest the inventive concepts provided herein are limited from fewer features, additional features, or alternative features to one or more of those features shown in FIGS. 1 to 15. For example, in various embodiments, the first arm 730, aperture 742, or endoluminal tool 746 of the guide device 700 shown in FIGS. 1 to 5 may include the shapes and features of the first arm 830, aperture 842, or endoluminal tool 846 of the guide device 800 shown described with reference to FIGS. 6 to 14D or the first arm 930, aperture 942, expandable portion 910, or inflatable member 902 of the guide device 900 shown described with reference to FIG. 15. It should also be understood that the reverse is true as well. One or more of the components depicted in FIGS. 6 to 14D or FIG. 15 can be employed in addition to, or as an alternative to components depicted in FIGS. 1 to 5. For example, the endoluminal tool 846 or deployment guide 852 of the guide device 800 shown in FIGS. 6 to 13 or FIGS. 14A to 14D may be employed in connection with the guide device 700 of FIGS. 1 to 5 or the guide device 900 shown in FIG. 15.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An endoluminal access device comprising:
an outer sheath defining a lumen;
a guide assembly including,
an expandable portion configured to self-expand from a collapsed configuration having a first diameter toward an expanded configuration having a second diameter that is greater than the first diameter, the expandable portion including:
a first arm including a tubular member defining a first lumen and an aperture in communication with the first lumen that is defined through a side wall of the tubular member, the aperture being positioned proximate a distal end of the first arm, and the expandable portion being configured to expand outwardly from a central longitudinal axis when the expandable portion transitions to the expanded configuration and to deflect inwardly toward the central longitudinal axis when the expandable portion is transitioned from the expanded configuration to the collapsed configuration; and
an inner shaft having a first end and a second end, the first arm coupled to the inner shaft proximate the second end of the inner shaft; and
an endoluminal tool deliverable from the first lumen of the first arm and outwardly from the aperture of the first arm.

2. The endoluminal access device of claim 1, wherein the endoluminal tool is slidably received within the first lumen.

3. The endoluminal access device of claim 1, wherein the endoluminal tool is slidably delivered from within the first lumen through the aperture.

4. The endoluminal access device of claim 1, wherein the first arm biases the endoluminal tool in a direction perpendicular to the central longitudinal axis of the expandable portion when the expandable portion is transitioned to the expanded configuration.

5. The endoluminal access device of claim 1, wherein the endoluminal tool is configured to exit the aperture at an acute angle relative to the central longitudinal axis of the expandable portion when the expandable portion is transitioned to the expanded configuration.

6. The endoluminal access device of claim 1, wherein in the expanded configuration the aperture orients the endoluminal tool at an escape angle relative to the central longitudinal axis of the expandable portion.

7. The endoluminal access device of claim 1, wherein in the expanded configuration the aperture orients the endoluminal tool at an escape angle from about 0 degrees to about 90 degrees relative to the central longitudinal axis of the expandable portion.

8. The endoluminal access device of claim 1, wherein in the expanded configuration the aperture is configured to orient the endoluminal tool at an escape angle of any one of about 0 degrees, about 10 degrees, about 20 degrees, about 30 degrees, about 40 degrees, about 50 degrees, about 60 degrees, about 70 degrees, about 80 degrees, or about 90 degrees.

9. The endoluminal access device of claim 1, wherein the endoluminal tool is a needle.

10. The endoluminal access device of claim 1, wherein the expandable portion is configured to confront a barrier located outward from the expandable portion when the expandable portion is transitioned to the expanded configuration.

11. The endoluminal access device of claim 1, wherein the expandable portion includes a plurality of arms that expand outwardly from the central longitudinal axis of the expandable portion when the expandable portion is transitioned to the expanded configuration.

12. The endoluminal access device of claim 11, wherein the plurality of arms is configured to expand symmetrically from the central longitudinal axis of the expandable portion.

13. The endoluminal access device of claim 11, wherein in the expanded configuration, each arm of the plurality of arms is spaced from another arm of the plurality of arms to define a plurality of open spaces between the plurality of arms.

14. The endoluminal access device of claim 11, wherein the expandable portion includes gaps between individual arms of the plurality of arms and defines an open interior space through which fluid can flow when the expandable portion is transitioned to the expanded configuration.

15. The endoluminal access device of claim 11, wherein the plurality of arms defines multiple lumens and wherein each lumen of the multiple lumens is configured to receive an endoluminal tool.

16. The endoluminal access device of claim 1, wherein fluid flow is maintained through a vessel with the endoluminal access device inserted within the vessel.

17. The endoluminal access device of claim 16, wherein each lumen of the multiple lumens is configured to be remotely deflected in-situ and position the endoluminal tool received within each lumen.

18. The endoluminal access device of claim 1, wherein the endoluminal tool is at least one of an infusion needle, a biopsy punch, a biopsy needle, an endotack, a suture device, a fixation device, a radiopaque marker, an occlusion coil, or a sensor.

19. A device for accessing a vessel surface from inside a vessel, the device having a central longitudinal axis and comprising:
an outer sheath defining a guide lumen;
a guide assembly slidably deployable from within the outer sheath and having an expandable portion including:
a plurality of arms, a first arm of the plurality of arms having a first end portion, a second end portion, a length, a wall defining a first lumen along the length, and an aperture in communication with the first lumen, the expandable portion self-expandable from a collapsed configuration with the first arm extending linearly along the central longitudinal axis toward an expanded configuration with a portion of the first arm expanded outward from the central longitudinal axis, the aperture located on the first arm such that in the expanded configuration the aperture is positioned on the portion of the first arm that is expanded outward from the central longitudinal axis; and
an inner shaft having a first end and a second end, the second end portion of the first arm coupled to the inner shaft proximate the second end of the inner shaft, wherein drawing the distal end of the inner shaft toward the first end portion of the first arm transitions the expandable portion to the expanded configuration.

20. The device of claim 19, wherein the first arm defines a free end at the second end portion and in the expanded configuration the second end portion is expanded outwardly from the central longitudinal axis greater than an outer diameter of the outer sheath.

21. The device of claim 19, wherein the first arm is configured to transition to the expanded configuration in response to the expandable portion being slidably advanced from within the outer sheath.

22. The device of claim 19, wherein the first arm has an intermediate portion between the first end portion and the second end portion, and wherein in the expanded configuration the intermediate portion expands outward from the central longitudinal axis to a greater extent than an outer diameter of the outer sheath.

23. The device of claim 19, further comprising a shaft portion connected to the expandable portion, the shaft portion defining an inner lumen and at least a first radial lumen, the inner shaft being slidably receivable within the inner lumen, and the first arm connected to the first radial lumen.

24. The device of claim 19, further comprising an endoluminal tool deployable from the first arm outward from the central longitudinal axis.

25. The device of claim 19, wherein the expandable portion is configured to deploy an endoluminal tool at an angle between 0 degrees and 90 degrees from the central longitudinal axis.

26. The device of claim 19, wherein fluid flow is maintained through a vessel with the device inserted within the vessel.

27. The device of claim 19, wherein the expandable portion includes gaps between individual arms of the plurality of arms and defines an open interior space through which fluid can flow when the expandable portion is transitioned to the expanded configuration.

* * * * *